US012582533B2

(12) United States Patent
Althobaiti et al.

(10) Patent No.:  US 12,582,533 B2
(45) Date of Patent:     Mar. 24, 2026

(54) INTEGRATED EXPANDABLE INTERBODY SPACER (IEIS)

(71) Applicant: IMAM ABDULRAHMAN BIN FAISAL UNIVERSITY, Dammam (SA)

(72) Inventors: Murad Althobaiti, Dammam (SA); Nasir Ghazi Hariri, Dammam (SA); Sajid Ali, Dammam (SA); Sultan Alsalmi, Dammam (SA)

(73) Assignee: IMAM ABDULRAHMAN BIN FAISAL UNIVERSITY, Dammam (SA)

( * ) Notice: Subject to any disclaimer, the term of this patent is extended or adjusted under 35 U.S.C. 154(b) by 11 days.

(21) Appl. No.: 18/799,592

(22) Filed: Aug. 9, 2024

(65)               Prior Publication Data
US 2026/0041563 A1      Feb. 12, 2026

(51) Int. Cl.
A61F 2/44 (2006.01)
A61F 2/30 (2006.01)

(52) U.S. Cl.
CPC .......... *A61F 2/4425* (2013.01); *A61F 2/3094* (2013.01); *A61F 2002/30062* (2013.01); *A61F 2002/30158* (2013.01); *A61F 2002/30263* (2013.01); *A61F 2002/30433* (2013.01); *A61F 2002/30507* (2013.01); *A61F 2002/30518* (2013.01); *A61F 2002/3055* (2013.01); *A61F 2002/30579* (2013.01); *A61F 2002/443* (2013.01)

(58) Field of Classification Search
CPC ............................... A61F 2/4455; A61F 2/447
See application file for complete search history.

(56)                References Cited

U.S. PATENT DOCUMENTS 8,574,300 B2    11/2013   McMANUS et al.
8,795,366 B2    8/2014    Varela
                (Continued)

OTHER PUBLICATIONS

"ProLift® Interbody Spacer System", ZimVie Inc., May 21, 2022, 8 pages.

(Continued)

*Primary Examiner* — Ellen C Hammond
(74) *Attorney, Agent, or Firm* — Oblon, McClelland, Maier & Neustadt, L.L.P.

(57)               ABSTRACT

An expandable interbody spacer including a first endplate and a second endplate, each with an outwardly facing surface, an inner facing surface, and two opposing isosceles-trapezoidal-shaped sidewalls. A motion assembly is located between the opposing sidewalls of both endplates, including a first motion guider with a smooth central cylindrical aperture, a second motion guider with a threaded central cylindrical aperture, and a screw with a screwhead and a partially threaded shank. The shank of the screw is positioned through the aperture in the first motion guider and into the aperture in the second motion guider. Clockwise rotation of the screwhead increases the height between the endplates by drawing the motion guiders together, while counterclockwise rotation decreases the height by moving them apart. The expandable interbody spacer permits controlled, in situ adjustment of height of the expandable interbody spacer to fit various intervertebral space requirements during spinal fusion procedures.

17 Claims, 9 Drawing Sheets

(56)          References Cited

U.S. PATENT DOCUMENTS

| 11,304,817 B2 | 4/2022 | Altarac et al. | |
| 11,752,007 B2 | 9/2023 | Spitler et al. | |
| 2020/0383798 A1* | 12/2020 | Butler | A61F 2/4455 |

OTHER PUBLICATIONS

Yan M. Li, et al., "Laterally Placed Expandable Interbody Spacers With and Without Adjustable Lordosis Improve Radiographic and Clinical Outcomes: a Two-Year Follow-up Study", Cureus 13(12): e20302, Dec. 9, 2021, 12 pages.

* cited by examiner

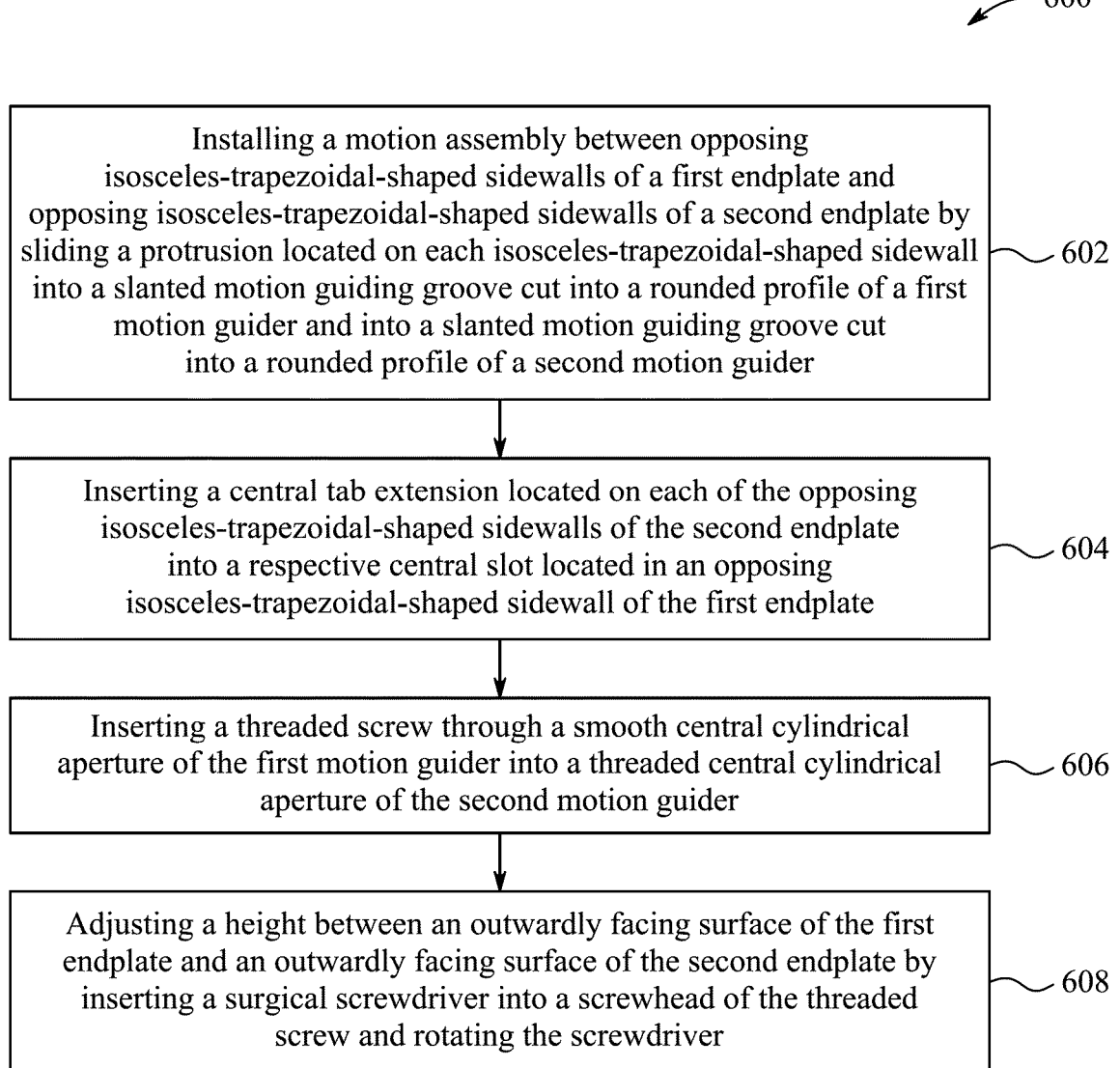

600

Installing a motion assembly between opposing isosceles-trapezoidal-shaped sidewalls of a first endplate and opposing isosceles-trapezoidal-shaped sidewalls of a second endplate by sliding a protrusion located on each isosceles-trapezoidal-shaped sidewall into a slanted motion guiding groove cut into a rounded profile of a first motion guider and into a slanted motion guiding groove cut into a rounded profile of a second motion guider                                              602

Inserting a central tab extension located on each of the opposing isosceles-trapezoidal-shaped sidewalls of the second endplate into a respective central slot located in an opposing isosceles-trapezoidal-shaped sidewall of the first endplate                                              604

Inserting a threaded screw through a smooth central cylindrical aperture of the first motion guider into a threaded central cylindrical aperture of the second motion guider                                              606

Adjusting a height between an outwardly facing surface of the first endplate and an outwardly facing surface of the second endplate by inserting a surgical screwdriver into a screwhead of the threaded screw and rotating the screwdriver                                              608

FIG. 6

INTEGRATED EXPANDABLE INTERBODY SPACER (IEIS)

BACKGROUND

Technical Field

The present disclosure is directed to spinal implants, and more specifically to an expandable interbody spacer for use in spinal fusion procedures, particularly in minimally invasive lateral lumbar interbody fusion operations.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Spinal fusion is a surgical procedure used to join two or more vertebrae in the spine. This procedure is often performed to alleviate pain and stabilize the spine in patients suffering from various spinal conditions, such as degenerative disc disease, spinal stenosis, or spondylolisthesis. In recent years, minimally invasive surgical techniques have gained popularity due to their potential for reduced postoperative pain, faster recovery times, and lower risk of complications. One such minimally invasive technique is lateral lumbar interbody fusion (LLIF), which approaches the spine from the side rather than from the front or back. This approach can minimize damage to the back muscles and nerves. In LLIF procedures, an interbody spacer is inserted between the vertebrae to maintain the proper height and alignment of the spine while fusion occurs.

Traditionally, these interbody spacers have been of a fixed size, requiring surgeons to choose the appropriate size before insertion. However, this can be challenging, as the intervertebral space may vary in size and shape. Expandable interbody spacers have emerged as a solution to this problem, allowing for in situ adjustment of the spacer height to better fit the patient's anatomy. Existing expandable spacers, however, often face limitations in terms of their expansion mechanism, stability, and ease of use. Some designs may not provide sufficient stability once expanded, while others may be difficult to adjust precisely during surgery. Additionally, there is a need for spacers that can adapt to the intervertebral architecture with minimal endplate disturbance and provide effective indirect decompression.

U.S. Pat. No. 11,752,007B2 describes an expandable intervertebral implant that includes an upper endplate and a lower endplate including a proximal end with a proximal ramp, and a distal end with a distal ramp respectively. The endplates have serrated outer surfaces and tapered inner structures. However, this reference does not mention use of any component to guide motion between the endplates.

U.S. Pat. No. 8,574,300B2 describes an expandable interbody spacer, including a superior component and an inferior component, each of which includes an endplate that provides a contact surface for engaging adjacent vertebra in an implanted position. The endplates of the superior component and the inferior component may include a series of teeth, ridges, spikes, keels, and/or surface texturing to increase the coefficient of friction between the endplates of the expandable interbody spacer and the adjacent vertebrae. However, this reference does not provide that the endplates have tapered structures which guide motion between the endplates.

Each of the aforementioned references suffers from one or more drawbacks hindering their adoption, such as limited adjustability, complex expansion mechanisms, potential instability at varying heights, and difficulty in achieving precise, controlled expansion in situ. Moreover, these devices lack effective locking mechanisms to maintain the desired expanded height. Accordingly, it is one object of the present disclosure to provide an expandable interbody spacer that provides improved adjustability, stability, and ease of use in minimally invasive procedures.

The present disclosure aims to overcome the limitations of the conventional spacers by incorporating a motion assembly with specially designed motion guiders and a screw-driven expansion mechanism, which allows for precise, controlled expansion after insertion, potentially reducing the risk of endplate damage during implantation and ensuring that the expandable interbody spacer maintains its expanded position.

SUMMARY

In an exemplary embodiment, an expandable interbody spacer is described. The expandable interbody spacer comprises a first endplate including an outwardly facing surface, an inner facing surface and two opposing isosceles-trapezoidal-shaped sidewalls each configured with a central slot; a second endplate including an outwardly facing surface and an inner facing surface and two opposing isosceles-trapezoidal-shaped sidewalls each configured with a central tab extension, wherein the second endplate is positioned directly opposite the first endplate; a motion assembly located between the opposing sidewalls of the first endplate and the opposing sidewalls of the second endplate, the motion assembly including: a first motion guider having a smooth central cylindrical aperture; a second motion guider having a threaded central cylindrical aperture; and a screw having a screwhead and a partially threaded shank, wherein the partially threaded shank is positioned through the smooth central cylindrical aperture of the first motion guider and into the threaded central cylindrical aperture of the second motion guider, wherein clockwise rotation of the screwhead is configured to increase a height between the first endplate and the second endplate by drawing the first motion guider and the second motion guider together; wherein counterclockwise rotation of the screwhead is configured to decrease a height between the first endplate and the second endplate by moving the first and second motion guiders apart.

In another exemplary embodiment, a method of assembling an expandable interbody spacer for use in lumbar interbody fusion is described. The method comprises installing a motion assembly between opposing isosceles-trapezoidal-shaped sidewalls of a first endplate and opposing isosceles-trapezoidal-shaped sidewalls of a second endplate by sliding a protrusion located on each isosceles-trapezoidal-shaped sidewall into a slanted motion guiding groove cut into a rounded profile of a first motion guider and into a slanted motion guiding groove cut into a rounded profile of a second motion guider; inserting a central tab extension located on each of the opposing isosceles-trapezoidal-shaped sidewalls of the second endplate into a respective central slot located in an opposing isosceles-trapezoidal-shaped sidewall of the first endplate; inserting a threaded screw through a smooth central cylindrical aperture of the first motion guider into a threaded central cylindrical aperture of the second motion guider; and adjusting a height between an outwardly facing surface of the first endplate and an outwardly facing surface of the second endplate by inserting a surgical screwdriver into a screwhead of the threaded screw and rotating the screwdriver.

In yet another exemplary embodiment, an expandable interbody spacer system is described. The expandable interbody spacer system comprises a first endplate including an outwardly facing surface, an inner facing surface and two opposing isosceles-trapezoidal-shaped sidewalls each configured with a central slot; a second endplate including an outwardly facing surface and an inner facing surface and two opposing isosceles-trapezoidal-shaped sidewalls each configured with a central tab extension, wherein the second endplate is positioned directly opposite the first endplate, wherein each central tab of the second endplate is configured to slide into a respective central slot of the first endplate; a motion assembly located between the opposing sidewalls of the first endplate and the opposing sidewalls of the second endplate, the motion assembly including: a first motion guider having a smooth central cylindrical aperture; a second motion guider having a threaded central cylindrical aperture; a surgical screwdriver; and a screw having a screwhead and a partially threaded shank, wherein the partially threaded shank is positioned through the smooth central cylindrical aperture of the first motion guider and into the threaded central cylindrical aperture of the second motion guider, wherein clockwise rotation of the screwhead by the surgical screwdriver is configured to increase a height between the first endplate and the second endplate by drawing the first motion guider and the second motion guider together, wherein counterclockwise rotation of the screwhead by the surgical screwdriver is configured to decrease a height between the first endplate and the second endplate by moving the first and second motion guiders apart.

The foregoing general description of the illustrative embodiments and the following detailed description thereof are merely exemplary aspects of the teachings of this disclosure and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein:

FIG. 6 is an exemplary flowchart of a method of assembling the expandable interbody spacer for use in lumbar interbody fusion, according to certain embodiments.

DETAILED DESCRIPTION

Figure 1A:
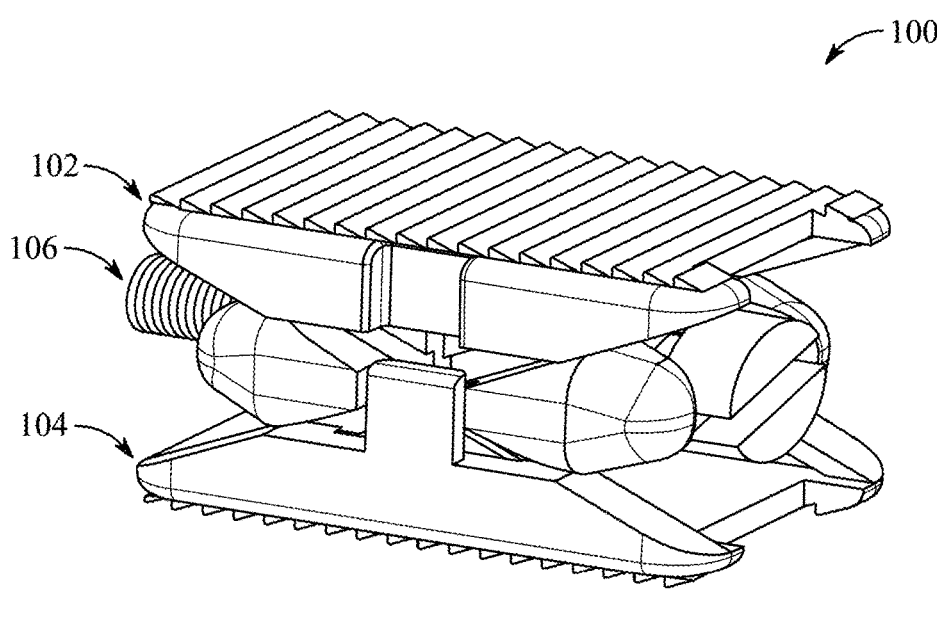
FIG. 1A is an exemplary perspective diagram of an expandable interbody spacer, according to certain embodiments.

In the drawings, like reference numerals designate identical or corresponding parts throughout the several views. Further, as used herein, the words "a", "an" and the like generally carry a meaning of "one or more", unless stated otherwise.

Furthermore, the terms "approximately," "approximate", "about" and similar terms generally refer to ranges that include the identified value within a margin of 20%, 10%, or preferably 5%, and any values therebetween.

Aspects of this disclosure are directed to an expandable interbody spacer, a method of assembling an expandable interbody spacer for use in lumbar interbody fusion, and an expandable interbody spacer system designed for use in spinal fusion procedures, particularly in minimally invasive lateral lumbar interbody fusion operations. The expandable interbody spacer includes endplates with tapered sidewalls and a motion assembly that can be inserted between the tapered sidewalls to expand or contract the spacer. The motion assembly includes a first motion guider, a second motion guider, and a screw. The screw can be rotated to move the motion guiders together or apart, thereby expanding or contracting the spacer. The expandable interbody spacer also includes central slots in the first endplate and central tab extensions in the second endplate. The central tab extensions are configured to slide into the central slots, providing additional stability to the assembled spacer.

Figure 1B:
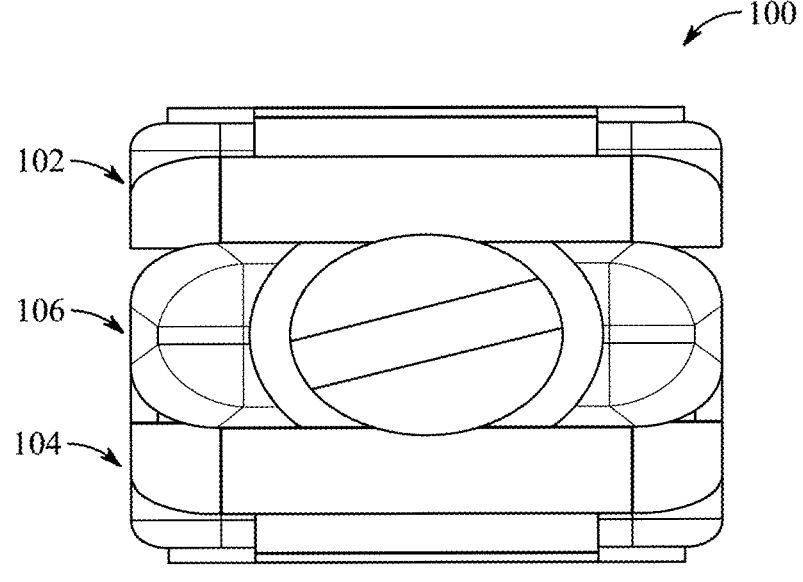
FIG. 1B is an exemplary front planar diagram of the expandable interbody spacer, according to certain embodiments.
Figure 1C:
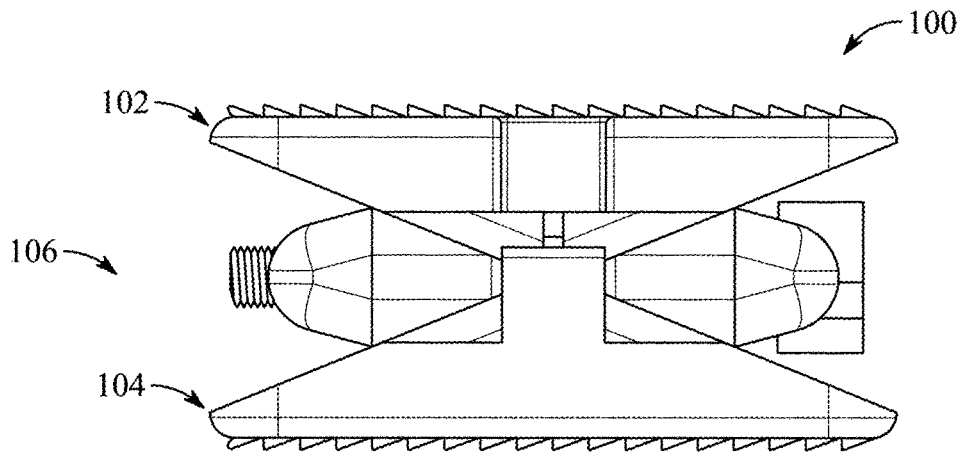
FIG. 1C is an exemplary side planar diagram of the expandable interbody spacer, according to certain embodiments.
Figure 1D:
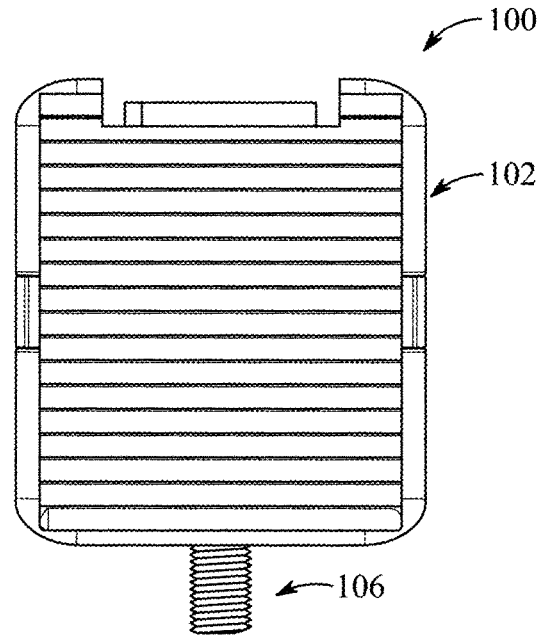
FIG. 1D is an exemplary top planar diagram of the expandable interbody spacer, according to certain embodiments.
Figure 1E:
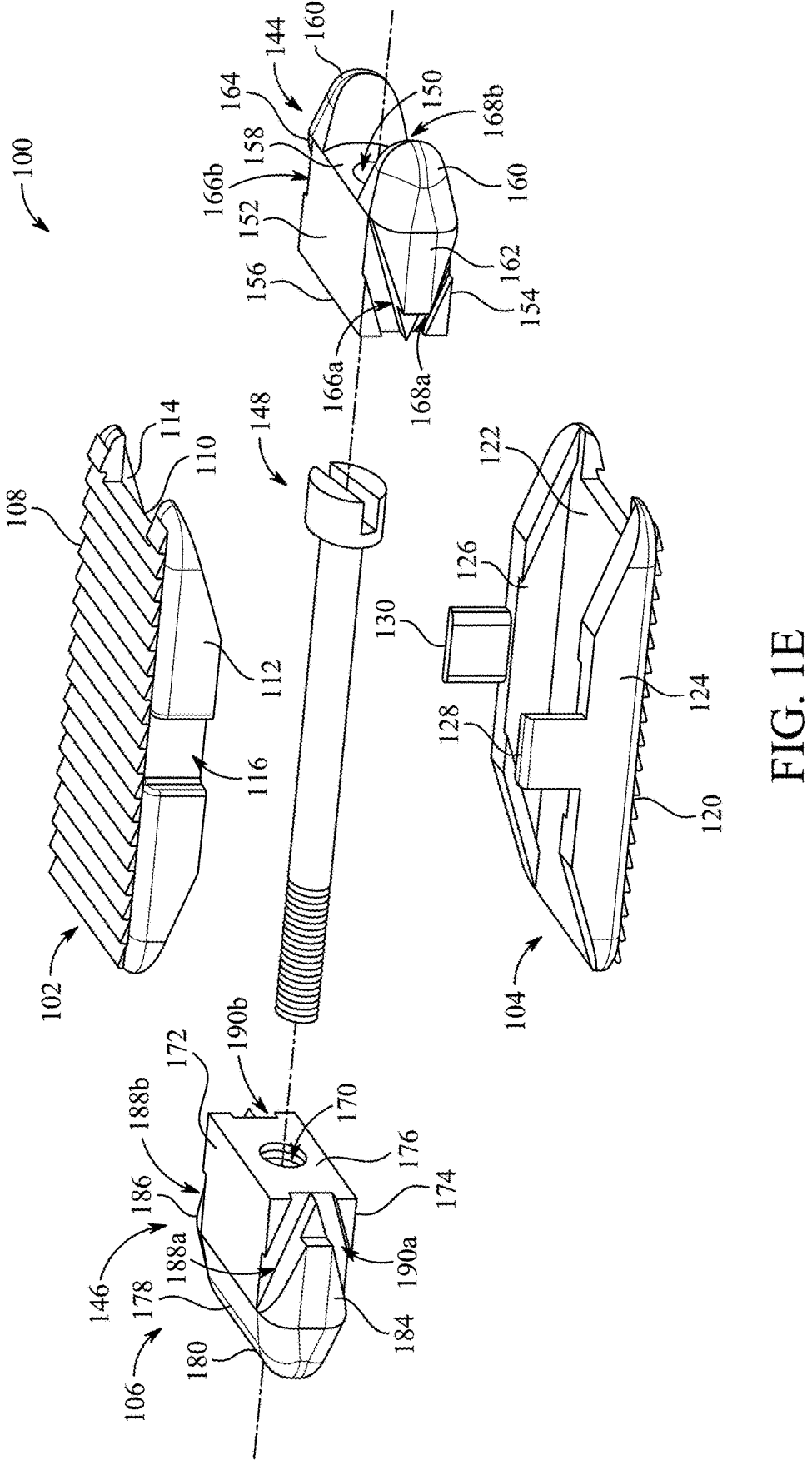
FIG. 1E is an exemplary exploded perspective diagram of the expandable interbody spacer, according to certain embodiments.

Referring to FIGS. 1A-1E in combination, illustrated are different views of an expandable interbody spacer (represented by reference numeral 100), also referred to as "integrated expandable interbody spacer" or IEIS. Herein, FIG. 1A is an exemplary perspective diagram of the expandable interbody spacer 100, FIG. 1B is an exemplary front planar diagram of the expandable interbody spacer 100, FIG. 1C is an exemplary side planar diagram of the expandable interbody spacer 100, FIG. 1D is an exemplary top planar diagram of the expandable interbody spacer 100, and FIG. 1E is an exemplary exploded perspective diagram of the expandable interbody spacer 100. The expandable interbody spacer 100 is a medical device designed for use in spinal fusion procedures, particularly in minimally invasive lateral lumbar interbody fusion (LLIF) operations. The expandable interbody spacer 100 is designed to be inserted between adjacent vertebrae in a compact form and subsequently expanded to an optimal height, allowing for precise adjustment to the patient's unique spinal anatomy. The expandable interbody spacer 100 incorporates an expansion mechanism that enables controlled, in situ adjustment of its height, potentially reducing the risk of endplate damage during insertion and improving the overall fit within the intervertebral space. The expandable interbody spacer 100 addresses challenges in spinal fusion procedures, including the need for minimally invasive insertion, precise height adjustment, stable fixation, and long-term reliability, and thus may be utilized in the treatment of various spinal conditions such as degenerative disc disease, spinal stenosis, and spondylolisthesis.

As illustrated, the expandable interbody spacer 100 includes a first endplate 102, a second endplate 104, and a motion assembly 106 located between the endplates 102, 104. The second endplate 104 is positioned directly opposite the first endplate 102. The first endplate 102 and the second endplate 104 are configured to accommodate and interact with the motion assembly 106, which is positioned between them. The motion assembly 106 is designed to facilitate the controlled expansion and contraction of the expandable interbody spacer 100 by enabling relative movement between the first endplate 102 and the second endplate 104. This arrangement allows for the adjustment of the overall height of the expandable interbody spacer 100, providing the capability to adapt to various intervertebral space requirements during spinal fusion procedures.

Figure 2A:
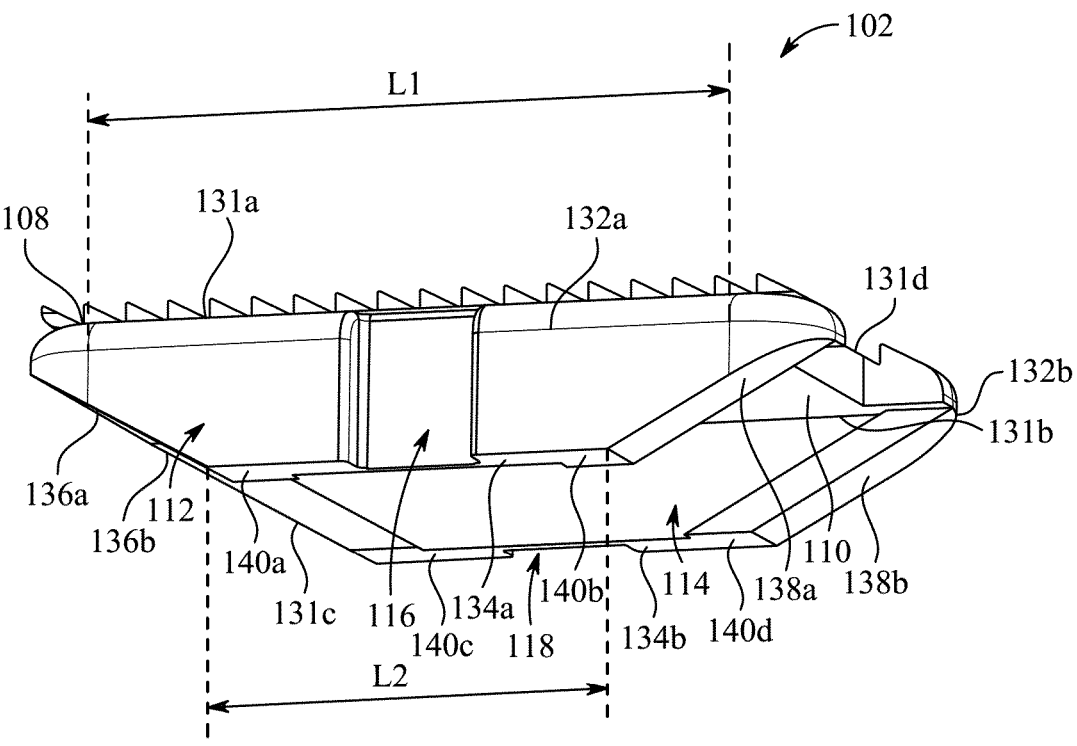
FIG. 2A is an exemplary perspective diagram of a first endplate of the expandable interbody spacer, according to certain embodiments.
Figure 2B:
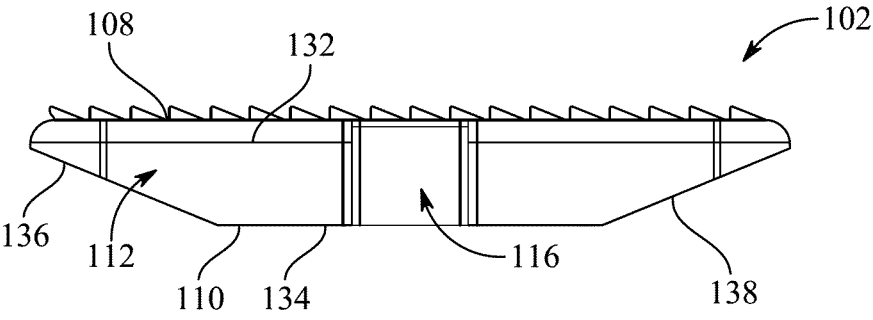
FIG. 2B is an exemplary side planar diagram of the first endplate, according to certain embodiments.

FIGS. 2A-2B illustrate detailed views of the first endplate 102. Herein, FIG. 2A is an exemplary perspective diagram of the first endplate 102 of the expandable interbody spacer 100, and FIG. 2B is an exemplary side planar diagram of the first endplate 102. As illustrated, the first endplate 102 includes an outwardly facing surface 108, an inner facing surface 110, and two opposing isosceles-trapezoidal-shaped sidewalls 112, 114. The outwardly facing surface 108 is designed to contact the vertebral endplate of a first vertebra of a patient. The inner facing surface 110 is configured to contact the motion assembly 106. Each of the two opposing isosceles-trapezoidal-shaped sidewalls 112, 114 of the first endplate 102 is configured with a central slot, including a central slot 116 on the isosceles-trapezoidal-shaped sidewall 112 and a central slot 118 on the isosceles-trapezoidal-shaped sidewall 114. These central slots 116, 118 are designed to receive extensions of the second endplate 104, as described in the following paragraphs.

In an aspect of the present disclosure, each central slot 116, 118 of the first endplate 102 has a width of about 3 mm, a height of about 7 mm, and a depth of about 1 mm. These dimensions may be adjusted based on the specific size and design requirements of the expandable interbody spacer 100. Further in an aspect of the present disclosure, the outwardly facing surface 108 of the first endplate 102 has a serrated profile to enhance engagement with the vertebral endplate and prevent migration of the expandable interbody spacer 100 after implantation. The serrated profile may have a pitch of about 1.0 mm, a height of about 0.5 mm, and a pitch angle of about 30 degrees. These dimensions may provide a balance between grip and bone integration. The number of serrations may vary, with one configuration having approximately 18 serrations on the outwardly facing surface 108.

Figure 3A:
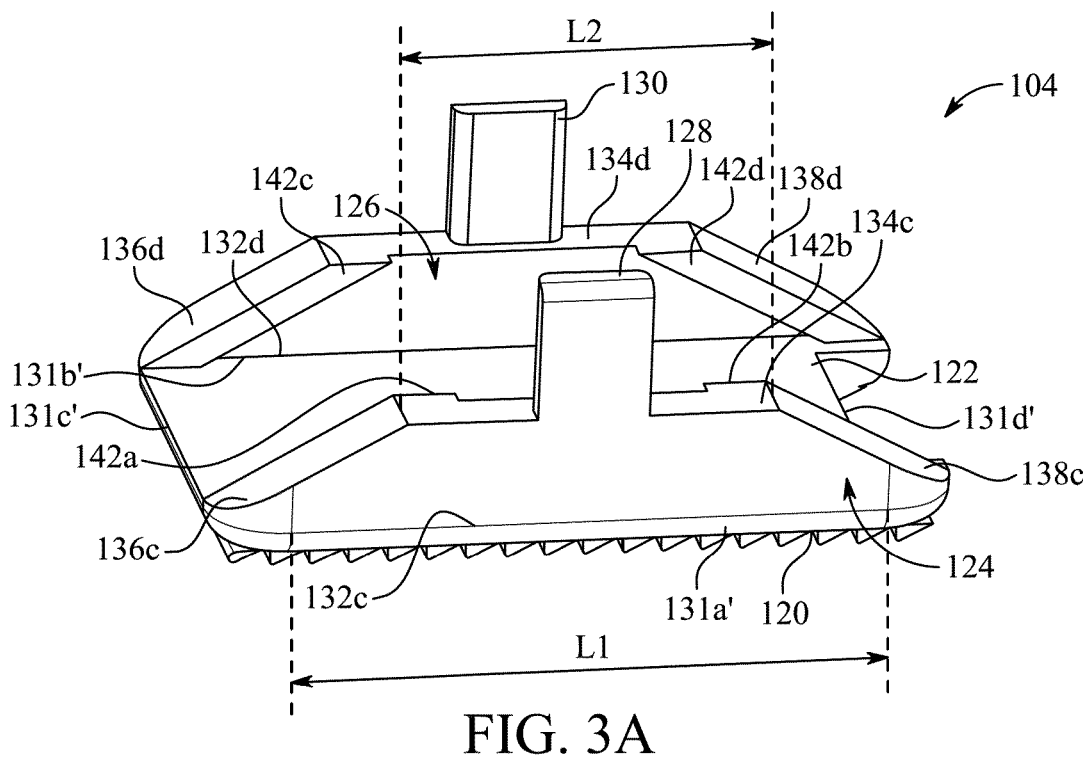
FIG. 3A is an exemplary perspective diagram of a second endplate of the expandable interbody spacer, according to certain embodiments.
Figure 3B:
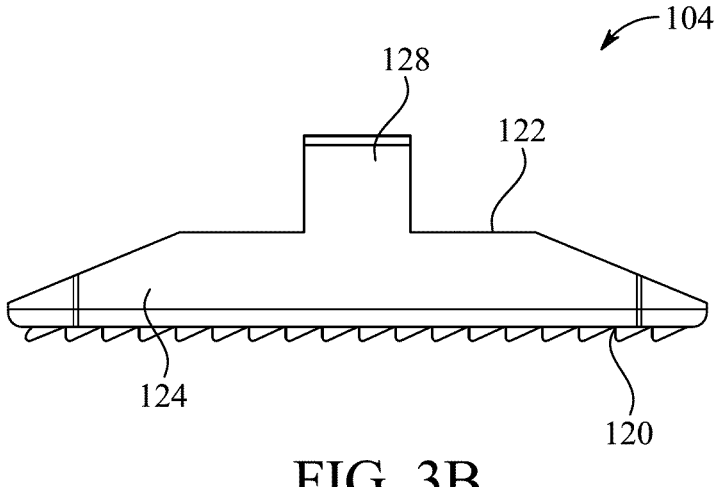
FIG. 3B is an exemplary side planar diagram of the second endplate, according to certain embodiments.

FIGS. 3A-3B illustrate detailed views of the second endplate 104. Herein, FIG. 3A is an exemplary perspective diagram of the second endplate 104 of the expandable interbody spacer 100, and FIG. 3B is an exemplary side planar diagram of the second endplate 104. The second endplate 104 includes an outwardly facing surface 120, an inner facing surface 122, and two opposing isosceles-trapezoidal-shaped sidewalls 124, 126. Similar to the first endplate 102, the outwardly facing surface 120 of the second endplate 104 is designed to contact the vertebral endplate of a second vertebra. Each of the two opposing isosceles-trapezoidal-shaped sidewalls 124, 126 of the second endplate 104 is configured with a central tab extension 128, 130 respectively. These central tab extensions 128, 130 are designed to be inserted into respective central slots 116, 118 of the first endplate 102. That is, the central slot 116 located in the opposing isosceles-trapezoidal-shaped sidewall 112 of the first endplate 102 is configured to receive the central tab extension 128 in the opposing isosceles-trapezoidal-shaped sidewall 124 of the second endplate 104, and the central slot 118 located in the opposing isosceles-trapezoidal-shaped sidewall 114 of the first endplate 102 is configured to receive the central tab extension 130 in the opposing isosceles-trapezoidal-shaped sidewall 126 of the second endplate 104. This arrangement provides a mechanism for guiding the relative movement of the endplates 102, 104 and maintaining their alignment during expansion and contraction of the expandable interbody spacer 100.

It may be understood that the central tab extensions 128, 130 in the second endplate 104 are designed to fit snugly into the respective central slots 116, 118 of the first endplate 102. This interlocking mechanism ensures that the endplates 102, 104 remain properly aligned throughout the range of motion, preventing any lateral shift or rotation that could compromise the stability of the expandable interbody spacer 100. In an aspect of the present disclosure, each central tab extension 128, 130 has a width of about 3 mm, a height of about 7 mm, and a depth of about 1 mm, in order to interlock with the respective central slot 116, 118 and to ensure a snug fit.

Further in an aspect of the present disclosure, the outwardly facing surface 120 also has a serrated profile. The serrated profile of the second endplate 104 may have similar specifications to that of the first endplate 102. That is, the serrated profile of the second endplate 104 may also have a pitch of about 1.0 mm, a height of about 0.5 mm and a pitch angle of about 30 degrees.

Referring to FIGS. 2A, 2B, 3A and 3B in combination, each endplate 102, 104 includes the serrated outwardly facing surface 108, 120 respectively, providing a textured profile that increases friction between the expandable interbody spacer 100 and the adjacent vertebral bodies. These serrated outwardly facing surfaces 108, 120 help prevent displacement of the expandable interbody spacer 100 after implantation, contributing to the overall stability of the spinal fusion. In contrast to the serrated outwardly facing surface 108, 120, the inner facing surface 110 of the respective endplate 102 and the inner facing surface 122 of the respective endplate 104 are smooth. These smooth inner facing surfaces 110, 122 facilitate efficient interaction with the motion assembly 106, reducing friction and wear during the expansion and contraction processes of the expandable interbody spacer 100.

Further, each endplate 102, 104 has a length and a width, with the length being greater than the width. This rectangular configuration is designed to match the typical anatomy of vertebral bodies.

As shown in FIG. 2A, the first endplate 102 includes a first edge 131a and a second edge 131b opposite to and parallel to the first edge 131a. Herein, the first edge 131a and the second edge 131b are located along the length of the first endplate 102. That is, along the length of the first endplate 102 are two parallel edges, including the first edge 131*a* and the second edge 131*b*, positioned opposite to each other. Further, the first endplate 102 includes a third edge 131*c* and a fourth edge 131*d* opposite to and parallel to the third edge 131*c*. Herein, the third edge 131*c* and the fourth edge 131*d* are located along the width of the respective endplate 102, 104. That is, along the width of the first endplate 102 are two parallel edges, including the third edge 131*c* and the fourth edge 131*d*, positioned opposite to each other.

Similarly, as shown in FIG. 3A, the second endplate 104 includes a first edge 131*a'* and a second edge 131*b'* opposite to and parallel to the first edge 131*a'*. Herein, the first edge 131*a'* and the second edge 131*b'* are located along the length of the second endplate 104. That is, along the length of the second endplate 104 are two parallel edges, including the first edge 131*a'* and a second edge 131*b'*, positioned opposite to each other. Further, the second endplate 104 includes a third edge 131*c'* and a fourth edge 131*d'* opposite to and parallel to the third edge 131*c'*. Herein, the third edge 131*c'* and the fourth edge 131*d'* are located along the width of the second endplate 104. That is, along the width of the second endplate 104 are two parallel edges, including the third edge 131*c'* and the fourth edge 131*d'*, positioned opposite to each other.

In the present configuration, the isosceles-trapezoidal shape of the sidewalls 112, 114, 124, 126 contribute to the overall stability and function of the expandable interbody spacer 100. Each of the isosceles-trapezoidal-shaped sidewalls 112, 114 of the first endplate 102 and the isosceles-trapezoidal-shaped sidewalls 124, 126 of the second endplate 104 includes design features that contribute to the functionality of the expandable interbody spacer 100.

As shown in FIG. 2A, the isosceles-trapezoidal-shaped sidewall 112 includes a first base 132*a* having a length L1, which is connected to the inner facing surface 110 of the corresponding first endplate 102. Opposite to the first base 132*a* is a second base 134*a* having a length L2. Herein, the length L1 of the first base 132*a* is greater than the length L2 of the second base 134*a*. Further, the first base 132*a* and the second base 134*a* are connected by two slanted legs, including a first slanted leg 136*a* and a second slanted leg 138*a*. The first slanted leg 136*a* is located between a first end of the first edge 131*a* and a first end of the second edge 131*b*, and the second slanted leg 138*a* is located between a second end of the first edge 131*a* and a second end of the second edge 131*b*. These slanted legs 136*a*, 138*a*, in conjunction with the unequal lengths L1 and L2 of the bases 132*a*, 134*a*, form the isosceles-trapezoidal shape of the isosceles-trapezoidal-shaped sidewall 112 in the first endplate 102.

Further, as shown in FIG. 2A, the isosceles-trapezoidal-shaped sidewall 114 similarly includes a first base 132*b* having a length L1, which is connected to the inner facing surface 110 of the corresponding first endplate 102. Opposite to the first base 132*b* is a second base 134*b* having a length L2. Herein, the length L1 of the first base 132*b* is greater than the length L2 of the second base 134*b*. Further, the first base 132*b* and the second base 134*b* are connected by two slanted legs, including a first slanted leg 136*b* and a second slanted leg 138*b*. The first slanted leg 136*b* is located between a first end of the first edge 131*a* and a first end of the second edge 131*b*, and the second slanted leg 138*b* is located between a second end of the first edge 131*a* and a second end of the second edge 131*b*. These slanted legs 136*b*, 138*b*, in conjunction with the unequal lengths L1 and L2 of the bases 132*b*, 134*b*, form the isosceles-trapezoidal shape of the isosceles-trapezoidal-shaped sidewall 114 in the first endplate 102.

Similarly, as shown in FIG. 3A, the isosceles-trapezoidal-shaped sidewall 124 includes a first base 132*c* having a length L1, which is connected to the inner facing surface 122 of the corresponding second endplate 104. Opposite to the first base 132*c* is a second base 134*c* having a length L2. Herein, the length L1 of the first base 132*c* is greater than the length L2 of the second base 134*c*. Further, the first base 132*c* and the second base 134*c* are connected by two slanted legs, including a first slanted leg 136*c* and a second slanted leg 138*c*. The first slanted leg 136*c* is located between a first end of the first edge 131*a'* and a first end of the second edge 131*b'*, and the second slanted leg 138*c* is located between a second end of the first edge 131*a'* and a second end of the second edge 131*b'*. These slanted legs 136*c*, 138*c*, in conjunction with the unequal lengths L1 and L2 of the bases 132*c*, 134*c*, form the isosceles-trapezoidal shape of the isosceles-trapezoidal-shaped sidewall 124 in the second endplate 104.

Further, as shown in FIG. 3A, the isosceles-trapezoidal-shaped sidewall 126 includes a first base 132*d* having a length L1, which is connected to the inner facing surface 122 of the corresponding second endplate 104. Opposite to the first base 132*d* is a second base 134*d* having a length L2. Herein, the length L1 of the first base 132*d* is greater than the length L2 of the second base 134*d*. Further, the first base 132*d* and the second base 134*d* are connected by two slanted legs, including a first slanted leg 136*d* and a second slanted leg 138*d*. The first slanted leg 136*d* is located between a first end of the first edge 131*a'* and a first end of the second edge 131*b'*, and the second slanted leg 138*d* is located between a second end of the first edge 131*a'* and a second end of the second edge 131*b'*. These slanted legs 136*d*, 138*d*, in conjunction with the unequal lengths L1 and L2 of the bases 132*d*, 134*d*, form the isosceles-trapezoidal shape of the isosceles-trapezoidal-shaped sidewall 126 in the second endplate 104.

Furthermore, as shown in FIG. 2A, the isosceles-trapezoidal-shaped sidewall 112 includes a protrusion 140*a* extending perpendicularly from the first slanted leg 136*a* towards the opposing sidewall 114, and a protrusion 140*b* extending perpendicularly from the second slanted leg 138*a* towards the opposing sidewall 114. Similarly, the isosceles-trapezoidal-shaped sidewall 114 includes a protrusion 140*c* extending perpendicularly from the first slanted leg 136*b* towards the opposing sidewall 112, and a protrusion 140*d* extending perpendicularly from the second slanted leg 138*b* towards the opposing sidewall 112. Also, as shown in FIG. 3A, the isosceles-trapezoidal-shaped sidewall 124 includes a protrusion 142*a* extending perpendicularly from the first slanted leg 136*c* towards the opposing sidewall 126, and a protrusion 142*b* extending perpendicularly from the second slanted leg 138*c* towards the opposing sidewall 126. Similarly, the isosceles-trapezoidal-shaped sidewall 126 includes a protrusion 142*c* extending perpendicularly from the first slanted leg 136*d* towards the opposing sidewall 124, and a protrusion 142*d* extending perpendicularly from the second slanted leg 138*d* towards the opposing sidewall 124. The protrusions 140*a-d*, 142*a-d* interact with design features (as discussed later) of the motion assembly 106 to cause vertical displacement of the endplates 102, 104, and thus facilitate the expansion mechanism of the expandable interbody spacer 100. The isosceles-trapezoidal shape of the sidewalls 112, 114, 124, 126, combined with the perpendicularly extending protrusions 140*a-d*, 142*a-d*, enables a controlled and stable expansion of the expandable interbody spacer 100. As the motion assembly 106 operates, these features guide the movement of the endplates 102, 104, ensuring that the expansion/contraction occurs in a controlled and secure manner.

Referring back to FIGS. 1A-1E, as shown, the motion assembly 106 is located between the opposing sidewalls 112, 114 of the first endplate 102 and the opposing sidewalls 124, 126 of the second endplate 104. This assembly is designed to facilitate the controlled expansion and contraction of the expandable interbody spacer 100. Herein, the motion assembly 106 includes a first motion guider 144, a second motion guider 146, and a screw 148. The first motion guider 144 and the second motion guider 146 are positioned between the endplates 102, 104 and interact with the protrusions 140a-d, 142a-d, shown in FIG. 2A. The screw 148 connects the first motion guider 144 and the second motion guider 146, allowing for their relative movement. When the screw 148 is rotated, it causes the motion guiders 144, 146 to move towards or away from each other, depending on the direction of rotation. This movement of the motion guiders 144, 146 translates into vertical displacement of the endplates 102, 104 through their interaction with the protrusions 140, 142 on the sidewalls 112, 114, 124, 126. The design of the motion assembly 106 allows for precise control over the height of the expandable interbody spacer 100, enabling it to be adjusted to fit various intervertebral space requirements.

Figures 4A, 4B:
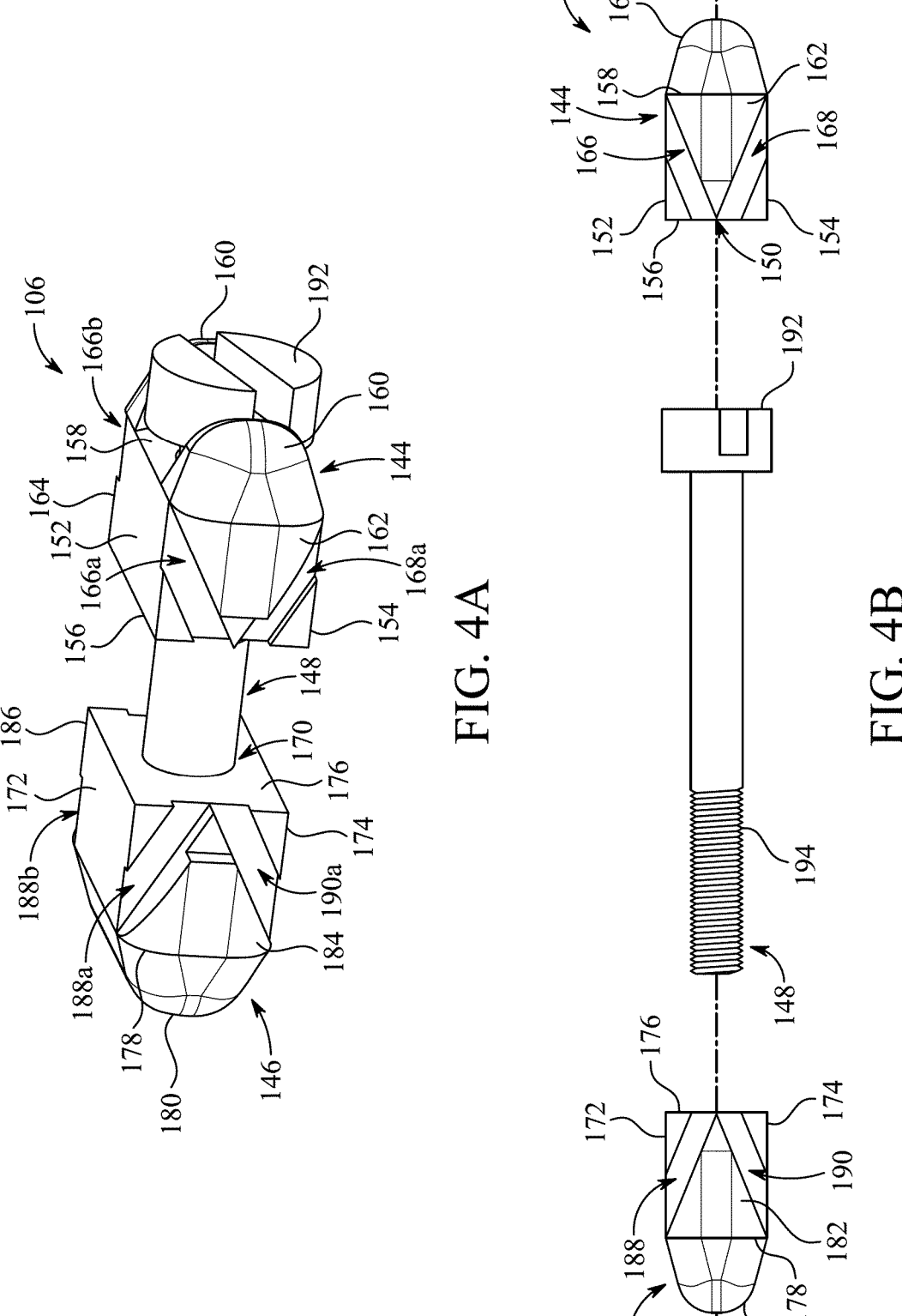
FIG. 4A is an exemplary assembled perspective diagram of a motion assembly of the expandable interbody spacer, according to certain embodiments.
FIG. 4B is an exemplary exploded side planar diagram of the motion assembly, according to certain embodiments.

FIGS. 4A-4B illustrate detailed views of the motion assembly 106. Herein, FIG. 4A is an exemplary assembled perspective diagram of the motion assembly 106 of the expandable interbody spacer 100, and FIG. 4B is an exemplary exploded side planar diagram of the motion assembly 106. In the motion assembly 106, the first motion guider 144 has a smooth central cylindrical aperture 150 (as better seen in FIG. 1E and generally represented in FIG. 4B). In an aspect, the first motion guider 144 has a rectangular cuboid body with a top face 152 and a bottom face 154. The top face 152 is specifically configured to contact the inner facing surface 110 of the first endplate 102. Similarly, the bottom face 154 is configured to contact the inner facing surface 122 of the second endplate 104. This direct contact between the first motion guider 144 and the endplates 102, 104 ensures efficient transfer of force during the expansion and contraction processes. The first motion guider 144 also includes a first wall 156 which includes the smooth central cylindrical aperture 150. The smooth central cylindrical aperture 150 is designed to partially accommodate the screw 148, allowing it to rotate freely within the first motion guider 144. The first wall 156 faces towards a corresponding first wall (as described later) of the second motion guider 146. The first motion guider 144 also includes a second wall 158 opposite to the first wall 156. The first motion guider 144 further includes a pair of bullet shaped endcaps 160 attached to either side of the second wall 158. The bullet shaped endcaps 160 extend outwardly from the motion assembly 106.

Further, the first motion guider 144 includes a third wall 162, and a fourth wall 164 opposite the third wall 162. The third wall 162 and the fourth wall 164 have rounded profiles and are located between the top face 152 and the bottom face 154. A pair of slanted motion guiding grooves, including a first slanted motion guiding groove 166a and a second slanted motion guiding groove 168a, are cut into the rounded profile of the third wall 162. Similarly, a pair of slanted motion guiding grooves, including a first slanted motion guiding groove 166b and a second slanted motion guiding groove 168b (not fully visible, but generally represented in FIG. 1E), are cut into the rounded profile of the fourth wall 164. Specifically, the first slanted motion guiding groove 166a is configured to slant from a central width axis of the first wall 156 towards the top face 152 near the second wall 158. The second motion guiding groove 168a is configured to slant from the central width axis of the first wall 156 towards the bottom face 154 near the second wall 158. Similarly, the first slanted motion guiding groove 166b is configured to slant from a central width axis of the first wall 156 towards the top face 152 near the second wall 158. The second motion guiding groove 168b is configured to slant from the central width axis of the first wall 156 towards the bottom face 154 near the second wall 158. These slanted motion guiding grooves 166a-b, 168a-b guide the movement of the endplates 102, 104 during expansion and contraction. Specifically, the protrusions 140b, 140d of the respective sidewalls 112, 114 of the first endplate 102 are configured to slide within the first slanted motion guiding grooves 166a, 166b respectively, while the protrusions 142b, 142d of the respective sidewalls 124, 126 of the second endplate 104 are configured to slide within the second slanted motion guiding grooves 168a, 168b respectively, of the first motion guider 144. This sliding interaction translates the horizontal motion of the first motion guider 144 into vertical displacement of the endplates 102, 104.

Again referring to FIGS. 4A-4B, in the motion assembly 106, the second motion guider 146 has a threaded central cylindrical aperture 170 (as better seen in FIG. 1E). In an aspect, the second motion guider 146 has a rectangular cuboid body with a top face 172 and a bottom face 174. The top face 172 is specifically configured to contact the inner facing surface 110 of the first endplate 102. Similarly, the bottom face 174 is configured to contact the inner facing surface 122 of the second endplate 104. This direct contact between the second motion guider 146 and the endplates 102, 104 ensures efficient transfer of force during the expansion and contraction processes. The second motion guider 146 also includes a first wall 176 configured to face towards the first wall 156 of the first motion guider 144. The second motion guider 146 also includes a second wall 178 opposite to the first wall 176. The threaded central cylindrical aperture 170 is located within the rectangular cuboid body between the first wall 176 and the second wall 178. The threaded central cylindrical aperture 170 is designed to partially accommodate and engage with the screw 148, allowing for the translation of rotational motion into linear motion. The second motion guider 146 further includes a rounded endcap 180 attached to either side of the second wall 178. The rounded endcap 180 extends outwardly from the motion assembly 106.

Further, the second motion guider 146 includes a third wall 184, and a fourth wall 186 opposite the third wall 184. The third wall 184 and the fourth wall 186 have rounded profiles and are located between the top face 172 and the bottom face 174. A pair of slanted motion guiding grooves, including a first slanted motion guiding groove 188a and a second slanted motion guiding groove 190a, are cut into the rounded profile of the third wall 184. Similarly, a pair of slanted motion guiding grooves, including a first slanted motion guiding groove 188b and a second slanted motion guiding groove 190b (not fully visible, but generally represented in FIG. 1E), are cut into the rounded profile of the fourth wall 186. Specifically, the first slanted motion guiding groove 188a is configured to slant from a central width axis of the first wall 176 towards the top face 172 near the second wall 178. The second motion guiding groove 190a is configured to slant from the central width axis of the first wall 176 towards the bottom face 174 near the second wall 178. Similarly, the first slanted motion guiding groove 188b is configured to slant from a central width axis of the first wall 156 towards the top face 152 near the second wall 158. The second motion guiding groove 190*b* is configured to slant from the central width axis of the first wall 156 towards the bottom face 154 near the second wall 158. These slanted motion guiding grooves 188*a-b*, 190*a-b* guide the movement of the endplates 102, 104 during expansion and contraction. Specifically, the protrusions 140*a*, 140*c* of the respective sidewalls 112, 114 of the first endplate 102 are configured to slide within the first slanted motion guiding groove 188*a*, 180*b* respectively, while the protrusions 142*a*, 142*c* of the sidewalls 124, 126 of the second endplate 104 are configured to slide within the second slanted motion guiding groove 190*a*, 190*b* respectively, of the second motion guider 146. This sliding interaction translates the horizontal motion of the second motion guider 146 into vertical displacement of the endplates 102, 104.

Furthermore, the screw 148 includes a screwhead 192 and a partially threaded shank 194. The screwhead 192 is designed to be easily accessible and manipulable by a surgical instrument, such as a screwdriver. The screwhead 192 may have a specific shape or indentation, such as a hexagonal recess, to allow for secure engagement with the screwdriver. This design enables precise control over the rotation of the screw 148 during the adjustment of the expandable interbody spacer 100. The partially threaded shank 194 is designed to be positioned through the smooth central cylindrical aperture 150 of the first motion guider 144 and into the threaded central cylindrical aperture 170 of the second motion guider 146. The smooth portion of the shank 194 allows for free rotation within the smooth central cylindrical aperture 150 of the first motion guider 144. This design ensures that the rotation of the screw 148 does not cause the first motion guider 144 to move longitudinally along the partially threaded shank 194. The threaded portion of the shank 194 engages with the threaded central cylindrical aperture 170 of the second motion guider 146 and cause the rotational motion of the screw 148 to be translated into linear motion of the second motion guider 146 relative to the first motion guider 144. Such design of the screw 148 and its interaction with the motion guiders 144, 146 allows for the expansion mechanism of the expandable interbody spacer 100.

Specifically, clockwise rotation of the screwhead 192 is configured to increase a height between the first endplate 102 and the second endplate 104 by drawing the first motion guider 144 and the second motion guider 146 together. That is, when the screwhead 192 is rotated clockwise, the threaded engagement causes the second motion guider 146 to be drawn towards the first motion guider 144. This movement of the motion guiders 144, 146 towards each other results in an increase in the height between the first endplate 102 and the second endplate 104. This occurs because the protrusions 140*a-d*, 142*a-d* on the respective sidewalls 112, 114, 124, 126 are forced to move along the corresponding slanted motion guiding grooves 166*a-b*, 168*a-b*, 188*a-b*, 190*a-b* in an upward direction. Conversely, counterclockwise rotation of the screwhead 192 is configured to decrease the height between the first endplate 102 and the second endplate 104 by moving the first and second motion guiders 144, 146 apart. In this case, the protrusions 140*a-d*, 142*a-d* on the respective sidewalls 112, 114, 124, 126 move along the corresponding slanted motion guiding grooves 166*a-b*, 168*a-b*, 188*a-b*, 190*a-b* in a downward direction.

In an aspect of the present disclosure, the screw 148 is a locking screw. This feature provides autolocking mechanism which ensures that the expandable interbody spacer 100 maintains its desired height after adjustment, preventing unintended collapse or expansion once implanted. The autolocking mechanism is inherent in the design of the motion assembly 106. Once adjusted to the desired height, the endplates 102, 104 cannot move downward by themselves due to the interaction between the protrusions 140*a-d*, 142*a-d* and the corresponding slanted motion guiding grooves 166*a-b*, 168*a-b*, 188*a-b*, 190*a-b*. The weight of the vertebrae pressing down on the endplates 102, 104 further enhances this locking effect, as it increases the friction between the protrusions 140*a-d*, 142*a-d* and the corresponding slanted motion guiding grooves 166*a-b*, 168*a-b*, 188*a-b*, 190*a-b*. Furthermore, the partially threaded nature of the shank 194 and its engagement with the threaded central cylindrical aperture 170 of the second motion guider 146 provides additional resistance against unintended movement. This combination of features ensures that the expandable interbody spacer 100 remains stable at its set height until intentionally adjusted by a surgeon.

In aspects of the present disclosure, the expandable interbody spacer 100 is made of biocompatible materials. Specifically, each of the first endplate 102, the second endplate 104 and the motion assembly 106 are formed of biocompatible materials. It may be appreciated that the expandable interbody spacer 100 is designed to be implanted in the human body for an extended period, and as such, it may be required that all of its components are made from materials that are compatible with the human body. The biocompatible materials are selected for their ability to resist corrosion, minimize adverse reactions in the body, and maintain their structural integrity over time. In an example, the biocompatible material used for the components of the expandable interbody spacer 100 is titanium. Titanium is widely used in medical implants due to its excellent biocompatibility. Titanium forms a stable oxide layer when exposed to air or bodily fluids, which contributes to its corrosion resistance. Titanium also has a high strength-to-weight ratio, making it ideal for use in the expandable interbody spacer 100 where both strength and lightness are desirable. In another example, the biocompatible material used for the components of the expandable interbody spacer 100 is polyetheretherketone (PEEK). PEEK is a high-performance thermoplastic polymer that has gained popularity in spinal implants due to its mechanical properties that are similar to bone, as well as its radiolucency which allows for easier postoperative imaging. The choice between titanium and PEEK may depend on various factors, including the specific patient needs, surgeon preference, and the particular requirements of the surgical procedure.

Further in aspects of the present disclosure, the expandable interbody spacer 100 has an assembled length which has a value in a range of about 15 mm to about 25 mm, an assembled width which has a value in a range of about 13 mm to about 15 mm and an assembled height which has a value of about 7 mm to about 24 mm. This range of assembled lengths allows the expandable interbody spacer 100 to adequately span the width of the vertebral endplates in the lumbar region, providing sufficient support and stability. This range in width provide a balance between adequate surface area for load distribution and the ability to insert the expandable interbody spacer 100 through a minimally invasive approach. Further, this wide range of potential heights is a key feature of the expandable interbody spacer 100 of the present disclosure, allowing it to accommodate various intervertebral disc heights and degrees of correction needed. The range of dimensions offered by the expandable interbody spacer 100 allows for its use in a variety of clinical scenarios, from mild disc degeneration to more severe cases requiring substantial height restoration. This versatility potentially reduces the need for multiple implant sizes to be stocked, streamlining inventory management for healthcare providers.

Figure 5A:
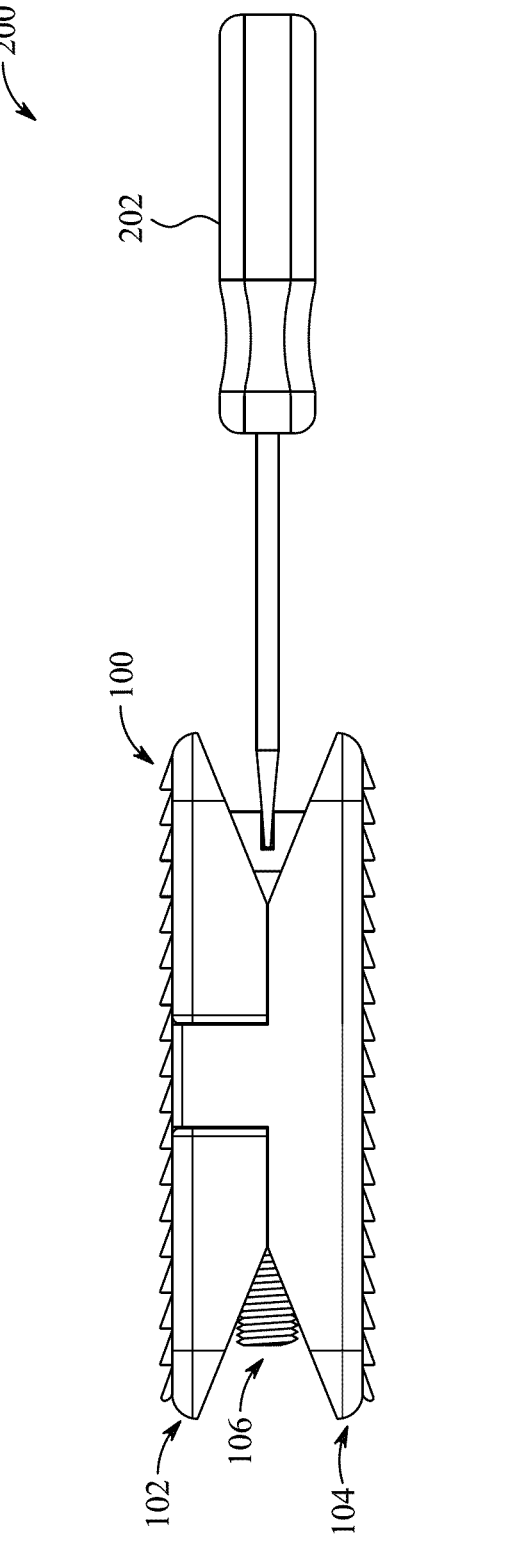
FIG. 5A is an exemplary diagram of an expandable interbody spacer system with the expandable interbody spacer in its contracted position, according to certain embodiments.
Figure 5B:
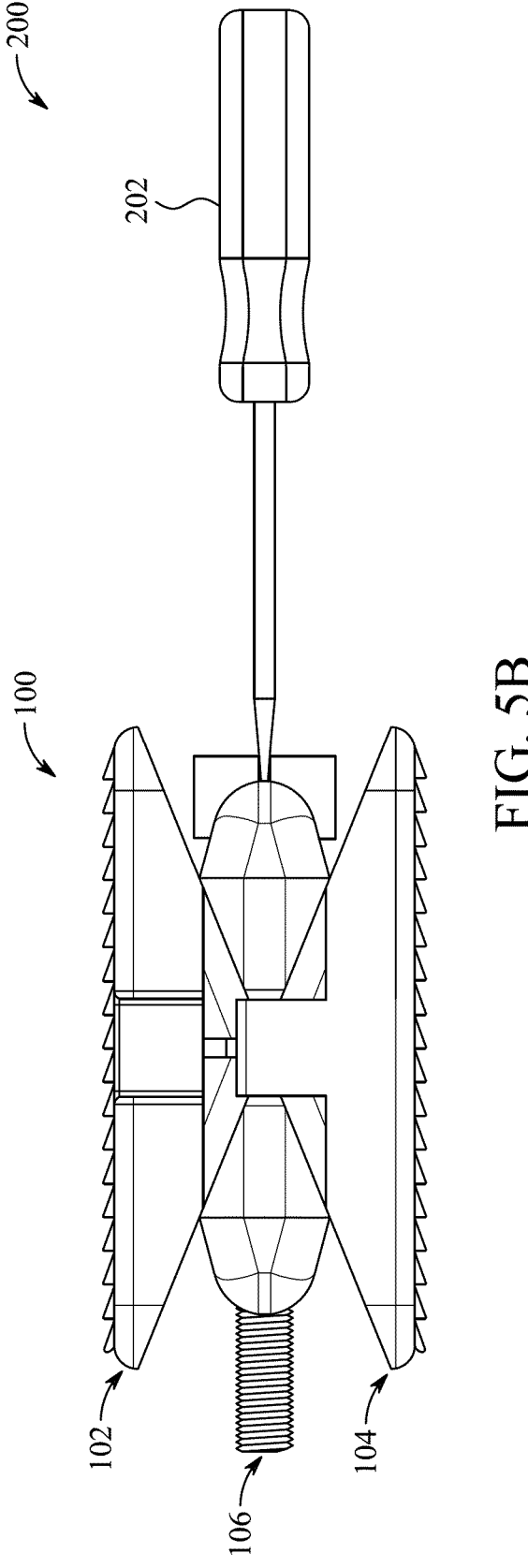
FIG. 5B is an exemplary diagram of the expandable interbody spacer system with the expandable interbody spacer in its expanded position, according to certain embodiments.

Referring now to FIGS. 5A and 5B, the present disclosure further provides an expandable interbody spacer system 200 for manipulating the expandable interbody spacer 100. FIG. 5A depicts the expandable interbody spacer system 200 with the expandable interbody spacer 100 in its contracted (closed) position, and FIG. 5B depicts the expandable interbody spacer system 200 with the expandable interbody spacer 100 in its expanded (open) position. As illustrated, the expandable interbody spacer system 200 comprises the expandable interbody spacer 100 and a surgical screwdriver 202. As described in the preceding paragraphs, the expandable interbody spacer 100 includes the first endplate 102 with the outwardly facing surface 108, the inner facing surface 110, and the two opposing isosceles-trapezoidal-shaped sidewalls 112, 114, each configured with the central slot 116, 118. The expandable interbody spacer system 200 also includes the second endplate 104 with the outwardly facing surface 120, the inner facing surface 122, and the two opposing isosceles-trapezoidal-shaped sidewalls 124, 126, each configured with the central tab extension 128, 130. The second endplate 104 is positioned directly opposite the first endplate 102, with the central tab extensions 128, 130 of the second endplate 104 configured to slide into the respective central slots 116, 118 of the first endplate 102.

Further, the expandable interbody spacer system 200 includes a motion assembly 106 located between the opposing sidewalls 112, 114 of the first endplate 102 and the opposing sidewalls 124, 126 of the second endplate 104. The motion assembly 106 includes the first motion guider 144 with the smooth central cylindrical aperture 150, and the second motion guider 146 with the threaded central cylindrical aperture 170. In the present configuration, the expandable interbody spacer system 200 includes the surgical screwdriver 202 as part thereof. The expandable interbody spacer system 200 also includes the screw 148, which has the screwhead 192 and the partially threaded shank 194. The partially threaded shank 194 is positioned through the smooth central cylindrical aperture 150 of the first motion guider 144 and into the threaded central cylindrical aperture 170 of the second motion guider 146.

The surgical screwdriver 202 is designed to engage with the screwhead 192 of the screw 148. When the surgical screwdriver 202 is used to rotate the screwhead 192 clockwise, it increases the height between the first endplate 102 and the second endplate 104 by drawing the first motion guider 144 and the second motion guider 146 together (as depicted in FIG. 5B). Conversely, when the surgical screwdriver 202 is used to rotate the screwhead 192 counterclockwise, it decreases the height between the first endplate 102 and the second endplate 104 by moving the first and second motion guiders 144, 146 apart (as depicted in FIG. 5A). This way the expandable interbody spacer system 200 allows for precise, controlled adjustment of the expandable interbody spacer 100 during surgical procedures, enabling surgeons to achieve optimal fit and alignment within the intervertebral space.

In an aspect of the present disclosure, the screwdriver 202 may be an electrically controlled screwdriver which receives drive current from a connected controller which generates the drive signals based on feedback from an imaging system, for example, an ultrasonic imager focused on the spine of the patient and on a surgical plan developed by a surgeon.

In the expandable interbody spacer system 200, the first motion guider 144 and the second motion guider 146 are designed with specific features to facilitate the controlled expansion and contraction of the expandable interbody spacer 100. The first motion guider 144 includes the rectangular cuboid body with the top face 152 and the bottom face 154. The top face 152 is configured to contact the inner facing surface 110 of the first endplate 102, while the bottom face 154 is configured to contact the inner facing surface 122 of the second endplate 104. The first motion guider 144 also includes the first wall 156 which includes the smooth central cylindrical aperture 150. The first wall 156 is oriented to face towards the corresponding first wall 176 of the second motion guider 146. Opposite to the first wall 156 is the second wall 158, to which the pair of bullet shaped endcaps 160 are attached. These bullet shaped endcaps 160 extend outwardly from the motion assembly 106.

The first motion guider 144 further includes the third wall 162 and the fourth wall 164, both having rounded profiles and located between the top face 152 and the bottom face 154. The pair of slanted motion guiding grooves 166a-b, 168a-b are cut into each of the rounded profiles of the third wall 162 and the fourth wall 164. The first slanted motion guiding grooves 166a, 166b are configured to slant from the central width axis of the first wall 156 towards the top face 152 near the second wall 158, while the second motion guiding grooves 168a, 168b are configured to slant from the central width axis of the first wall 156 towards the bottom face 154 near the second wall 158. These slanted motion guiding grooves 166a-b, 168a-b are designed to accommodate the respective protrusions 140a-d, 142a-d. Specifically, the protrusions 140b, 140d of the respective sidewalls 112, 114 of the first endplate 102 are configured to slide within the first slanted motion guiding grooves 166a, 166b respectively, while the protrusions 142b, 142d of the respective sidewalls 124, 126 of the second endplate 104 are configured to slide within the second slanted motion guiding groove 168a, 168b respectively, of the first motion guider 144.

The second motion guider 146 has the similar structure to the first motion guider 144, with some key differences. The second motion guider 146 also has the rectangular cuboid body with the top face 172 and the bottom face 174, configured to contact the inner facing surfaces 110, 122 of the first and second endplates 102, 104 respectively. The second motion guider 146 has the first wall 176 that faces towards the first wall 156 of the first motion guider 144, and the second wall 178 opposite to the first wall 176. The threaded central cylindrical aperture 170 is located within the rectangular cuboid body between the first wall 176 and the second wall 178. Herein, instead of bullet shaped endcaps, the second motion guider 146 includes the rounded endcap 180 attached to either side of the second wall 178, extending outwardly from the motion assembly 106. Also, similar to the first motion guider 144, the second motion guider 146 includes the third wall 184 and the fourth wall 186 with rounded profiles, located between the top face 172 and the bottom face 174. These walls 184, 186 also include slanted motion guiding grooves 188a-b, 190a-b cut into their rounded profiles, functioning in the same manner as those in the first motion guider 144. The protrusions 140a, 140c, 142a, 142c of the respective sidewalls 112, 114, 124, 126 are configured to slide within these grooves 188a-b, 190a-b, facilitating the controlled expansion and contraction of the expandable interbody spacer 100.

Referring now to FIG. 6, the present disclosure further provides a method (as represented by a flowchart, referred by reference numeral 600) of assembling the expandable interbody spacer 100 for use in lumbar interbody fusion. The method 600 includes a series of steps. These steps are only illustrative, and other alternatives may be considered where one or more steps are added, one or more steps are removed, or one or more steps are provided in a different sequence without departing from the scope of the present disclosure. Various variants disclosed above, with respect to the afore-mentioned expandable interbody spacer 100 and the expand-able interbody spacer system 200 apply mutatis mutandis to the present method 600.

At step 602, the method 600 involves installing the motion assembly 106 between the opposing isosceles-trap-ezoidal-shaped sidewalls 112, 114 of the first endplate 102 and the opposing isosceles-trapezoidal-shaped sidewalls 124, 126 of the second endplate 104. This is accomplished by sliding the protrusions 140a-d located on the respective isosceles-trapezoidal-shaped sidewalls 112, 114 of the first endplate 102 into the corresponding first slanted motion guiding grooves 166a-b, 188a-b cut into the rounded profile of the respective third walls 162, 184 and the fourth walls 164, 186 of the first motion guider 144 and the second motion guider 146 respectively. Similarly, the protrusions 142a-d located on the respective isosceles-trapezoidal-shaped sidewalls 124, 126 of the second endplate 104 is slid into the corresponding second slanted motion guiding grooves 168a-b, 190a-b of the first motion guider 144 and the second motion guider 146 respectively.

At step 604, the method 600 involves inserting the central tab extensions 128, 130 located on the respective opposing isosceles-trapezoidal-shaped sidewalls 124, 126 of the sec-ond endplate 104 into the corresponding central slots 116, 118 located in the respective opposing isosceles-trapezoidal-shaped sidewalls 112, 114 of the first endplate 102. This step ensures proper alignment and connection between the first endplate 102 and the second endplate 104. Further at step 606, the method 600 involves inserting the threaded screw 148 through the smooth central cylindrical aperture 150 of the first motion guider 144 and into the threaded central cylindrical aperture 170 of the second motion guider 146. This step establishes the expansion mechanism of the expandable interbody spacer 100.

Finally, at step 608, the method 600 involves adjusting the height between the outwardly facing surface 108 of the first endplate 102 and the outwardly facing surface 120 of the second endplate 104. This adjustment is performed by inserting the surgical screwdriver 202 into the screwhead 192 of the threaded screw 148 and rotating the screwdriver 202. The direction of rotation determines whether the height increases or decreases, allowing for precise adjustment of the expandable interbody spacer 100 to fit the specific requirements of the intervertebral space. When the surgical screwdriver 202 is used to rotate the screwhead 192 clock-wise, it increases the height between the first endplate 102 and the second endplate 104 by drawing the first motion guider 144 and the second motion guider 146 together. Conversely, when the surgical screwdriver 202 is used to rotate the screwhead 192 counterclockwise, it decreases the height between the first endplate 102 and the second end-plate 104 by moving the first and second motion guiders 144, 146 apart.

In one scenario, the method 600 may be implemented for expanding the height between the first endplate 102 and the second endplate 104. This is accomplished by inserting the surgical screwdriver 202 between the pair of bullet shaped endcaps 160 of the first motion guider 144 to access the screwhead 192 of the screw 148. The surgeon then rotates the screwhead 192 in a clockwise direction using the surgical screwdriver 202. This clockwise rotation causes the first motion guider 144 and the second motion guider 146 to be drawn together. As the motion guiders 144, 146 come closer, the protrusions 140a-d, 142a-d on the respective sidewalls 112, 114, 124, 126 of the endplates 102, 104 slide along the slanted motion guiding grooves 166a-b, 168a-b, 188a-b, 190a-b. This sliding motion results in an increase in the vertical distance between the first endplate 102 and the second endplate 104, effectively expanding the height of the expandable interbody spacer 100.

In another scenario, the method 600 may be implemented for contracting the height between the first endplate 102 and the second endplate 104. This process is similar to the expansion process but in reverse. For this purpose, the surgical screwdriver 202 is inserted between the pair of bullet shaped endcaps 160 to engage with the screwhead 192. However, in this case, the surgeon rotates the screw-head 192 in a counterclockwise direction. This counter-clockwise rotation forces the first motion guider 144 and the second motion guider 146 to move apart. As the motion guiders 144, 146 separate, the protrusions 140a-d, 142a-d on the respective sidewalls 112, 114, 124, 126 of the endplates 102, 104 slide along the slanted motion guiding grooves 166a-b, 168a-b, 188a-b, 190a-b. This sliding motion results in a decrease in the vertical distance between the first endplate 102 and the second endplate 104, effectively con-tracting the height of the expandable interbody spacer 100.

The method 600 further comprises additional steps that detail the surgical procedure for implanting and adjusting the expandable interbody spacer 100 within a patient's spine. Initially, the method 600 involves removing one or more of a disk and a lamina from between two vertebrae of a spine of a patient. This step is typically performed to create space for the expandable interbody spacer 100. Following the tissue removal, the method 600 proceeds with inserting the expandable interbody spacer 100 between the two ver-tebrae. The expandable interbody spacer 100 is oriented so that the serrated outwardly facing surface 108 of the first endplate 102 faces a first vertebra, while the serrated out-wardly facing surface 120 of the second endplate 104 faces a second vertebra of the two vertebrae. Once the expandable interbody spacer 100 is properly positioned, the method 600 involves expanding the height between the first endplate 102 and the second endplate 104. This is achieved by inserting the surgical screwdriver 202 between the pair of bullet shaped endcaps 160 to access the screwhead 192 of the screw 148. The surgeon then rotates the screwhead 192 in a clockwise direction using the surgical screwdriver 202. This clockwise rotation causes the first motion guider 144 and the second motion guider 146 to be drawn together, effectively expanding the height of the expandable interbody spacer 100. The surgeon continues this expansion process until the desired height is achieved. This procedure allows for pre-cise, controlled expansion of the expandable interbody spacer 100 in situ, enabling the surgeon to ensure proper fit and alignment within the intervertebral space.

The method 600 further comprises additional steps that detail an alternative surgical procedure for implanting and adjusting the expandable interbody spacer 100 within a patient's spine. Initially, the method 600 involves removing a disk from between two vertebrae of a spine of a patient. This step is typically performed to create space for the expandable interbody spacer 100 and to address the under-lying spinal condition. Following the disk removal, the method 600 proceeds with inserting the rounded endcap 180 of the expandable interbody spacer 100 between the two vertebrae. The expandable interbody spacer 100 is oriented so that the serrated outwardly facing surface 108 of the first endplate 102 faces a first vertebra, while the serrated outwardly facing surface 120 of the second endplate 104 faces a second vertebra of the two vertebrae. The rounded endcap 180 facilitates smooth insertion of the expandable interbody spacer 100 by gently parting the surrounding tissues. Once the expandable interbody spacer 100 is properly positioned, the method 600 involves contracting the height between the first endplate 102 and the second endplate 104. This is achieved by inserting the surgical screwdriver 202 between the pair of bullet shaped endcaps 160 to access the screwhead 192 of the screw 148. The surgeon then rotates the screwhead 192 in a counterclockwise direction using the surgical screwdriver 202. This counterclockwise rotation forces the first motion guider 144 and the second motion guider 146 to move apart, effectively contracting the height of the expandable interbody spacer 100. The surgeon continues this contraction process until the desired height is achieved, which is typically determined by the restoration of proper disc height and spinal alignment. This procedure allows for precise, controlled contraction of the expandable interbody spacer 100 in situ, enabling the surgeon to ensure proper fit and alignment within the intervertebral space.

The expandable interbody spacer 100 is designed for minimally invasive insertion, particularly in lateral lumbar interbody fusion (LLIF) procedures. The insertion process typically involves the following steps. The expandable interbody spacer 100 is initially set to its minimum height configuration, with the endplates 102, 104 at their closest position. The surgeon creates a small incision and establishes a pathway to the intervertebral space, typically using a series of dilators. The damaged disc material is removed from the intervertebral space, preparing it for the expandable interbody spacer 100. The expandable interbody spacer 100 is then inserted into the prepared intervertebral space. Once positioned correctly, the expandable interbody spacer 100 is expanded to the desired height. This is achieved by inserting the long, straight surgical screwdriver 200 through the incision and engaging it with the screwhead 192. The surgeon then rotates the screwdriver 200 clockwise to expand the expandable interbody spacer 100. The surgeon continues to adjust the height of the expandable interbody spacer 100 until optimal fit and spinal alignment are achieved. This can be verified through intraoperative imaging. Once the desired height is reached, the autolocking mechanism ensures that the expandable interbody spacer 100 maintains its expanded position. The surgical screwdriver is then removed, and the incision is closed. This minimally invasive approach, combined with the ability to adjust the expandable interbody spacer 100 in situ, potentially reduces trauma to surrounding tissues and allows for more precise fitting of the spacer to the patient's anatomy.

The expandable interbody spacer 100 of the present disclosure incorporates isosceles-trapezoidal-shaped sidewalls on both the first endplate 102 and the second endplate 104, each including protrusions 140_a-d_, 142_a-d_ respectively, that interact with the corresponding slanted motion guiding grooves 166_a-b_, 168_a-b_, 188_a-b_, 190_a-b_ on the first motion guider 144 and the second motion guider 146. This configuration, combined with the screw-driven expansion mechanism, allows for precise and controlled adjustment of the spacer height after insertion into the intervertebral space. The use of the smooth central cylindrical aperture 150 in the first motion guider 144 and the threaded central cylindrical aperture 170 in the second motion guider 146, through which the partially threaded shank 194 of the screw 148 is positioned, ensures a more stable and controlled expansion mechanism. The inclusion of the central tab extensions 128, 130 on the second endplate 104 that slide into the central slots 116, 118 on the first endplate 102 provides additional stability and alignment during the expansion process. Furthermore, the bullet shaped endcaps 160 and rounded endcap 180 facilitate smoother insertion of the expandable interbody spacer 100 into the intervertebral space.

A first embodiment describes an expandable interbody spacer 100, comprising a first endplate 102 including an outwardly facing surface 108, an inner facing surface 110 and two opposing isosceles-trapezoidal-shaped sidewalls 112, 114 each configured with a central slot 116, 118; a second endplate 104 including an outwardly facing surface 120 and an inner facing surface 122 and two opposing isosceles-trapezoidal-shaped sidewalls 124, 126 each configured with a central tab extension 128, 130, wherein the second endplate 104 is positioned directly opposite the first endplate 102; a motion assembly 106 located between the opposing sidewalls 112, 114 of the first endplate 102 and the opposing sidewalls 124, 126 of the second endplate 104, the motion assembly 106 including a first motion guider 144 having a smooth central cylindrical aperture 150; a second motion guider 146 having a threaded central cylindrical aperture 170; and a screw 148 having a screwhead 192 and a partially threaded shank 194, wherein the partially threaded shank 194 is positioned through the smooth central cylindrical aperture 150 of the first motion guider 144 and into the threaded central cylindrical aperture 170 of the second motion guider 146, wherein clockwise rotation of the screwhead 192 is configured to increase a height between the first endplate 102 and the second endplate 104 by drawing the first motion guider 144 and the second motion guider 146 together; wherein counterclockwise rotation of the screwhead 192 is configured to decrease a height between the first endplate 102 and the second endplate 104 by moving the first and second motion guiders 144, 146 apart.

In an aspect, each central slot 116, 118 located in an opposing isosceles-trapezoidal-shaped sidewall 112, 114 of the first endplate 102 is configured to receive a respective central tab extension 128, 130 of the second endplate 104.

In an aspect, each central slot 116, 118 has a width of about 3 mm, a height of about 7 mm and a depth of about 1 mm.

In an aspect, the screw 148 is a locking screw.

In an aspect, each of the first endplate 102, the second endplate 104 and the motion assembly 106 are formed of biocompatible materials.

In an aspect, the biocompatible material is titanium.

In an aspect, the biocompatible material is polyetheretherketone PEEK. the outwardly facing surface 108 of the first endplate 102 has a serrated profile; and the outwardly facing surface 120 of the second endplate 104 has a serrated profile.

In an aspect, the serrated profile of each of the first endplate 102 and the second endplate 104 has a pitch of about 1.0 mm, a height of about 0.5 mm and a pitch angle of about 30 degrees.

In an aspect, each endplate 102, 104 comprises the serrated outwardly facing surface 108, 120; the inner facing surface 110, 122, wherein the inner facing surface 110, 122 is smooth; a length and a width, wherein the length is greater than the width; a first edge 131_a_, 131_a'_; a second edge 131_b_, 131_b'_ opposite to and parallel to the first edge 131_a_, 131_a'_, wherein the first edge 131_a_, 131_a'_ and the second edge 131_b_, 131_b'_ are located along the length; a third edge 131_c_, 131_c'_; and a fourth edge 131_d_, 131_d'_ opposite to and parallel to the third edge 131*c*, 131*c*', wherein the third edge 131*c*, 131*c*' and the fourth edge 131*d*, 131*d*' are located along the width, wherein each of the isosceles-trapezoidal-shaped sidewalls 112, 114, 124, 126 includes a first base 132*a-d* having a length L1, wherein the first base 132*a-d* is connected to the inner facing surface 110, 122 of a respective endplate 102, 104, a second base 134*a-d* having a length L2, wherein the length L1 is greater than the length L2, a first slanted leg 136*a-d* located between a first end of the first edge 131*a*, 131*a*' and a first end of the second edge 131*b*, 131*b*', a second slanted leg 138*a-d* located between a second end of the first edge 131*a*, 131*a*' and a second end of the second edge 131*b*, 131*b*', and a protrusion 140*a-d*, 142*a-d* extending perpendicularly from each of the first slanted leg 136*a-d* and the second slanted leg 138*a-d* towards the opposing sidewall.

In an aspect, the first motion guider 144 further comprises a rectangular cuboid body having a top face 152 configured to contact the inner facing surface 110 of the first endplate 102; a bottom face 154 configured to contact the inner facing surface 122 of the second endplate 104; a first wall 156 which includes the smooth central cylindrical aperture 150, wherein the first wall 156 faces towards a first wall 176 of the second motion guider 146; a second wall 158 opposite the first wall 156; a pair of bullet shaped endcaps 160 attached to the second wall 158, wherein the pair of bullet shaped endcaps 160 extends outwardly from the motion assembly 106; a third wall 162 having a rounded profile; a fourth wall 164 having a rounded profile opposite the third wall 162, wherein the third wall 162 and the fourth wall 164 are located between the top face 152 and the bottom face 154; and a pair of slanted motion guiding grooves 166*a-b*, 168*a-b* cut into each of the rounded profile of the third wall 162 and the rounded profile of the fourth wall 164, wherein a first slanted motion guiding groove 166*a-b* is configured to slant from a central width axis of the first wall 156 towards the top face 152 near the second wall 158, and a second motion guiding groove 168*a-b* is configured to slant from a central width axis of the first wall 156 towards the bottom face 154 near the second wall 158, wherein a respective protrusion 140*b*, 140*d* of a sidewall 112, 114 of the first endplate 102 is configured to slide within the first slanted motion guiding groove 166*a-b* and a respective protrusion 142*b*, 142*d* of a sidewall 124, 126 of the second endplate 104 is configured to slide within the second slanted motion guiding groove 168*a-b* of the first motion guider 144.

In an aspect, the second motion guider 146 further comprises a rectangular cuboid body having a top face 172 configured to contact the inner facing surface 110 of the first endplate 102; a bottom face 174 configured to contact the inner facing surface 122 of the second endplate 104; a first wall 176 configured to face towards a first wall 156 of the first motion guider 144; a second wall 178 opposite the first wall 176, wherein the threaded central cylindrical aperture 170 is located within the rectangular cuboid body between the first wall 176 and the second wall 178; a rounded endcap 180 attached to either side of the second wall 178, wherein the rounded endcap 180 extends outwardly from the motion assembly 106; a third wall 184 having a rounded profile; a fourth wall 186 having a rounded profile opposite the third wall 184, wherein the third wall 184 and the fourth wall 186 are located between the top face 172 and the bottom face 174; and a pair of slanted motion guiding grooves 188*a-b*, 190*a-b* cut into each of the rounded profile of the third wall 184 and the rounded profile of the fourth wall 186, wherein a first slanted motion guiding groove 188*a-b* is configured to slant from a central width axis of the first wall 176 towards the top face 172 near the second wall 178, and a second motion guiding groove 190*a-b* is configured to slant from a central width axis of the first wall 176 towards the bottom face 174 near the second wall 178, wherein a respective protrusion 140*a*, 140*c* of a sidewall 112, 114 of the first endplate 102 is configured to slide within the first slanted motion guiding groove 188*a-b* and a respective protrusion 142*a*, 142*c* of a sidewall 124, 126 of the second endplate 104 is configured to slide within the second slanted motion guiding groove 190*a-b* of the second motion guider 146.

In an aspect, an assembled length has a value in a range of about 15 mm to about 25 mm, an assembled width has a value in a range of about 13 mm to about 15 mm and an assembled height has a value of about 7 mm to about 24 mm.

A second embodiment describes a method 600 of assembling an expandable interbody spacer 100 for use in lumbar interbody fusion, comprising installing a motion assembly 106 between opposing isosceles-trapezoidal-shaped sidewalls 112, 114 of a first endplate 102 and opposing isosceles-trapezoidal-shaped sidewalls 124, 126 of a second endplate 104 by sliding a protrusion 140*a-d*, 142*a-d* located on each isosceles-trapezoidal-shaped sidewall 112, 114, 124, 126 into a slanted motion guiding groove 166*a-b*, 168*a-b* cut into a rounded profile of a first motion guider 144 and into a slanted motion guiding groove 188*a-b*, 190*a-b* cut into a rounded profile of a second motion guider 146; inserting a central tab extension 128, 130 located on each of the opposing isosceles-trapezoidal-shaped sidewalls 124, 126 of the second endplate 104 into a respective central slot 116, 118 located in an opposing isosceles-trapezoidal-shaped sidewall 112, 114 of the first endplate 102; inserting a threaded screw 148 through a smooth central cylindrical aperture 150 of the first motion guider 144 into a threaded central cylindrical aperture 170 of the second motion guider 146; and adjusting a height between an outwardly facing surface 108 of the first endplate 102 and an outwardly facing surface 120 of the second endplate 104 by inserting a surgical screwdriver 202 into a screwhead 192 of the threaded screw 148 and rotating the screwdriver 202.

In an aspect, the method 600 further comprises expanding a height between the first endplate 102 and the second endplate 104 by inserting the surgical screwdriver 202 between a pair of bullet shaped endcaps 160 into the screwhead 192 and rotating the screwhead 192 in a clockwise direction to draw the first motion guider 144 and the second motion guider 146 together by sliding along the slanted motion guiding grooves 166*a-b*, 168*a-b*, 188*a-b*, 190*a-b*.

In an aspect, the method 600 further comprises contracting a height between the first endplate 102 and the second endplate 104 by inserting the surgical screwdriver 202 between a pair of bullet shaped endcaps 160 into the screwhead 192 and rotating the screwhead 192 a counterclockwise direction to force the first motion guider 144 and the second motion guider 146 apart by sliding along the slanted motion guiding grooves 166*a-b*, 168*a-b*, 188*a-b*, 190*a-b*.

In an aspect, the method 600 further comprises removing one or more of a disk and a lamina from between two vertebrae of a spine of a patient; inserting the expandable interbody spacer 100 between the two vertebrae so that a serrated outwardly facing surface 108 of the first endplate 102 faces a first vertebrae and a serrated outwardly facing surface 120 of the second endplate 104 faces a second vertebrae of the two vertebrae; and expanding a height between the first endplate 102 and the second endplate 104 by rotating, by the surgical screwdriver 202, the screwhead 192 in a clockwise direction to draw the first motion guider 144 and the second motion guider 146 together.

In an aspect, the method 600 further comprises removing a disk from between two vertebrae of a spine of a patient; inserting a rounded endcap 180 of the expandable interbody spacer 100 between the two vertebrae so that a serrated outwardly facing surface 108 of the first endplate 102 faces a first vertebrae and a serrated outwardly facing surface 120 of the second endplate 104 faces a second vertebrae of the two vertebrae; and contracting a height between the first endplate 102 and the second endplate 104 by rotating, by the surgical screwdriver 202, the screwhead 192 in a counter-clockwise direction to force the first motion guider 144 and the second motion guider 146 apart.

A third embodiment describes an expandable interbody spacer system 200, comprising a first endplate 102 including an outwardly facing surface 108, an inner facing surface 110 and two opposing isosceles-trapezoidal-shaped sidewalls 112, 114 each configured with a central slot 116, 118; a second endplate 104 including an outwardly facing surface 120 and an inner facing surface 122 and two opposing isosceles-trapezoidal-shaped sidewalls 124, 126 each con-figured with a central tab extension 128, 130, wherein the second endplate 104 is positioned directly opposite the first endplate 102, wherein each central tab extension 128, 130 of the second endplate 104 is configured to slide into a respec-tive central slot 116, 118 of the first endplate 102; a motion assembly 106 located between the opposing sidewalls 112, 114 of the first endplate 102 and the opposing sidewalls 124, 126 of the second endplate 104, the motion assembly 106 including a first motion guider 144 having a smooth central cylindrical aperture 150; a second motion guider 146 having a threaded central cylindrical aperture 170; a surgical screw-driver 202; and a screw 148 having a screwhead 192 and a partially threaded shank 194, wherein the partially threaded shank 194 is positioned through the smooth central cylin-drical aperture 150 of the first motion guider 144 and into the threaded central cylindrical aperture 170 of the second motion guider 146, wherein clockwise rotation of the scre-whead 192 by the surgical screwdriver 202 is configured to increase a height between the first endplate 102 and the second endplate 104 by drawing the first motion guider 144 and the second motion guider 146 together, wherein coun-terclockwise rotation of the screwhead 192 by the surgical screwdriver 202 is configured to decrease a height between the first endplate 102 and the second endplate 104 by moving the first and second motion guiders 144, 146 apart.

In an aspect, the first motion guider 144 further comprises a rectangular cuboid body having a top face 152 configured to contact the inner facing surface 110 of the first endplate 102; a bottom face 154 configured to contact the inner facing surface 122 of the second endplate 104; a first wall 156 which includes the smooth central cylindrical aperture 150, wherein the first wall 156 faces towards a first wall 176 of the second motion guider 146; a second wall 158 opposite the first wall 156; a pair of bullet shaped endcaps 160 attached to the second wall 158, wherein the pair of bullet shaped endcaps 160 extends outwardly from the motion assembly 106; a third wall 162 having a rounded profile; a fourth wall 164 having a rounded profile opposite the third wall 162, wherein the third wall 162 and the fourth wall 164 are located between the top face 152 and the bottom face 154; a pair of slanted motion guiding grooves 166a-b, 168a-b cut into each of the rounded profile of the third wall 162 and the rounded profile of the fourth wall 164, wherein a first slanted motion guiding groove 166a-b is configured to slant from a central width axis of the first wall 156 towards the top face 152 near the second wall 158, and a second motion guiding groove 168a-b is configured to slant from a central width axis of the first wall 156 towards the bottom face 154 near the second wall 158, wherein a respective protrusion 140b, 140d of a sidewall 112, 114 of the first endplate 102 is configured to slide within the first slanted motion guiding groove 166a-b and a respective protrusion 142b, 142d of a sidewall 124, 126 of the second endplate 104 is configured to slide within the second slanted motion guiding groove 168a-b of the first motion guider 144; the second motion guider 146 further comprises a rectangular cuboid body having a top face 172 configured to contact the inner facing surface 110 of the first endplate 102; a bottom face 174 configured to contact the inner facing surface 122 of the second endplate 104; a first wall 176 configured to face towards a first wall 156 of the first motion guider 144; a second wall 178 opposite the first wall 176, wherein the threaded central cylindrical aperture 170 is located within the rectangular cuboid body between the first wall 176 and the second wall 178; a rounded endcap 180 attached to either side of the second wall 178, wherein the rounded endcap 180 extends outwardly from the motion assembly 106; a third wall 184 having a rounded profile; a fourth wall 186 having a rounded profile opposite the third wall 184, wherein the third wall 184 and the fourth wall 186 are located between the top face 172 and the bottom face 174; and a pair of slanted motion guiding grooves 188a-b, 190a-b cut into each of the rounded profile of the third wall 184 and the rounded profile of the fourth wall 186, wherein a first slanted motion guiding groove 188a-b is configured to slant from a central width axis of the first wall 176 towards the top face 172 near the second wall 178, and a second motion guiding groove 190a-b is configured to slant from a central width axis of the first wall 176 towards the bottom face 174 near the second wall 178, wherein a respective protrusion 140a, 140c of a sidewall 112, 114 of the first endplate 102 is configured to slide within the first slanted motion guiding groove 188a-b and a respective protrusion 142a, 142c of a sidewall 124, 126 of the second endplate 104 is configured to slide within the second slanted motion guiding groove 190a-b of the second motion guider 146.

Numerous modifications and variations of the present disclosure are possible in light of the above teachings. It is therefore to be understood that within the scope of the appended claims, the invention may be practiced otherwise than as specifically described herein.

The invention claimed is:

1. An expandable interbody spacer, comprising:
a first endplate including an outwardly facing surface, an inner facing surface and two opposing isosceles-trap-ezoidal-shaped sidewalls each configured with a central slot;
a second endplate including an outwardly facing surface and an inner facing surface and two opposing isosceles-trapezoidal-shaped sidewalls each configured with a central tab extension, wherein the second endplate is positioned directly opposite the first endplate; and
a motion assembly located between the opposing side-walls of the first endplate and the opposing sidewalls of the second endplate, the motion assembly including:
a first motion guider having a smooth central cylindri-cal aperture;
a second motion guider having a threaded central cylindrical aperture; and
a screw having a screwhead and a partially threaded shank, wherein the partially threaded shank is posi-tioned through the smooth central cylindrical aperture of the first motion guider and into the threaded central cylindrical aperture of the second motion guider, wherein clockwise rotation of the screwhead is configured to increase a height between the first endplate and the second endplate by drawing the first motion guider and the second motion guider together;

wherein counterclockwise rotation of the screwhead is configured to decrease a height between the first endplate and the second endplate by moving the first and second motion guiders apart; and wherein the first motion guider further comprises:

a rectangular cuboid body having a top face configured to contact the inner facing surface of the first endplate;

a bottom face configured to contact the inner facing surface of the second endplate;

a first wall which includes the smooth central cylindrical aperture, wherein the first wall faces towards a first wall of the second motion guider;

a second wall opposite the first wall;

a pair of bullet shaped endcaps attached to the second wall, wherein the pair of bullet shaped endcaps extends outwardly from the motion assembly;

a third wall having a rounded profile;

a fourth wall having a rounded profile opposite the third wall, wherein the third wall and the fourth wall are located between the top face and the bottom face; and a pair of slanted motion guiding grooves cut into each of the rounded profile of the third wall and the rounded profile of the fourth wall, wherein a first slanted motion guiding groove is configured to slant from a central width axis of the first wall towards the top face near the second wall, and a second motion guiding groove is configured to slant from a central width axis of the first wall towards the bottom face near the second wall, wherein a respective protrusion of a sidewall of the first endplate is configured to slide within the first slanted motion guiding groove and a respective protrusion of a sidewall of the second endplate is configured to slide within the second slanted motion guiding groove of the first motion guider.

2. The expandable interbody spacer of claim 1, wherein each central slot located in an opposing isosceles-trapezoidal-shaped sidewall of the first endplate is configured to receive a respective central tab extension of the second endplate.

3. The expandable interbody spacer of claim 1, wherein each central slot has a width of about 3 mm, a height of about 7 mm and a depth of about 1 mm.

4. The expandable interbody spacer of claim 1, wherein the screw is a locking screw.

5. The expandable interbody spacer of claim 1, wherein each of the first endplate, the second endplate and the motion assembly are formed of biocompatible materials.

6. The expandable interbody spacer of claim 5, wherein the biocompatible material is titanium.

7. The expandable interbody spacer of claim 5, wherein the biocompatible material is polyetheretherketone (PEEK).

8. The expandable interbody spacer of claim 1, wherein:

the outwardly facing surface of the first endplate has a serrated profile; and the outwardly facing surface of the second endplate has a serrated profile.

9. The expandable interbody spacer of claim 8, wherein the serrated profile of each of the first endplate and the second endplate has a pitch of about 1.0 mm, a height of about 0.5 mm and a pitch angle of about 30 degrees.

10. The expandable interbody spacer of claim 8, wherein each endplate comprises:

the serrated outwardly facing surface;

the inner facing surface, wherein the inner facing surface is smooth;

a length and a width, wherein the length is greater than the width;

a first edge;

a second edge opposite to and parallel to the first edge, wherein the first edge and the second edge are located along the length;

a third edge; and a fourth edge opposite to and parallel to the third edge, wherein the third edge and the fourth edge are located along the width, wherein each of the isosceles-trapezoidal-shaped sidewalls includes:

a first base having a length L1, wherein the first base is connected to the inner facing surface of a respective endplate, a second base having a length L2, wherein the length L1 is greater than the length L2, a first slanted leg located between a first end of the first edge and a first end of the second edge, a second slanted leg located between a second end of the first edge and a second end of the second edge, and a protrusion extending perpendicularly from each of the first slanted leg and the second slanted leg towards the opposing sidewall.

11. The expandable interbody spacer of claim 1, wherein the second motion guider further comprises:

a rectangular cuboid body having a top face configured to contact the inner facing surface of the first endplate;

a bottom face configured to contact the inner facing surface of the second endplate;

a first wall configured to face towards a first wall of the first motion guider;

a second wall opposite the first wall, wherein the threaded central cylindrical aperture is located within the rectangular cuboid body between the first wall and the second wall;

a rounded endcap attached to either side of the second wall, wherein the rounded endcap extends outwardly from the motion assembly;

a third wall having a rounded profile;

a fourth wall having a rounded profile opposite the third wall, wherein the third wall and the fourth wall are located between the top face and the bottom face; and a pair of slanted motion guiding grooves cut into each of the rounded profile of the third wall and the rounded profile of the fourth wall, wherein a first slanted motion guiding groove is configured to slant from a central width axis of the first wall towards the top face near the second wall, and a second motion guiding groove is configured to slant from a central width axis of the first wall towards the bottom face near the second wall, wherein a respective protrusion of a sidewall of the first endplate is configured to slide within the first slanted motion guiding groove and a respective protrusion of a sidewall of the second endplate is configured to slide within the second slanted motion guiding groove of the second motion guider.

12. The expandable interbody spacer of claim 1, wherein an assembled length has a value in a range of about 15 mm to about 25 mm, an assembled width has a value in a range of about 13 mm to about 15 mm and an assembled height has a value of about 7 mm to about 24 mm.

13. A method of assembling an expandable interbody spacer for use in lumbar interbody fusion, comprising:

installing a motion assembly between opposing isosceles-trapezoidal-shaped sidewalls of a first endplate and opposing isosceles-trapezoidal-shaped sidewalls of a second endplate by sliding a protrusion located on each isosceles-trapezoidal-shaped sidewall into a slanted motion guiding groove cut into a rounded profile of a first motion guider and into a slanted motion guiding groove cut into a rounded profile of a second motion guider;

inserting a central tab extension located on each of the opposing isosceles-trapezoidal-shaped sidewalls of the second endplate into a respective central slot located in an opposing isosceles-trapezoidal-shaped sidewall of the first endplate;

inserting a threaded screw through a smooth central cylindrical aperture of the first motion guider into a threaded central cylindrical aperture of the second motion guider;

adjusting a height between an outwardly facing surface of the first endplate and an outwardly facing surface of the second endplate by inserting a surgical screwdriver into a screwhead of the threaded screw and rotating the screwdriver; and expanding a height between the first endplate and the second endplate by inserting the surgical screwdriver between a pair of bullet shaped endcaps into the screwhead and rotating the screwhead in a clockwise direction to draw the first motion guider and the second motion guider together by sliding along the slanted motion guiding grooves.

14. The method of claim 13, comprising:

contracting a height between the first endplate and the second endplate by inserting the surgical screwdriver between a pair of bullet shaped endcaps into the screwhead and rotating the screwhead a counterclockwise direction to force the first motion guider and the second motion guider apart by sliding along the slanted motion guiding grooves.

15. The method of claim 13, comprising:

removing one or more of a disk and a lamina from between two vertebrae of a spine of a patient;

inserting the expandable interbody spacer between the two vertebrae so that a serrated outwardly facing surface of the first endplate faces a first vertebrae and a serrated outwardly facing surface of the second endplate faces a second vertebrae of the two vertebrae; and expanding a height between the first endplate and the second endplate by rotating, by the surgical screwdriver, the screwhead in a clockwise direction to draw the first motion guider and the second motion guider together.

16. The method of claim 13, comprising:

removing a disk from between two vertebrae of a spine of a patient;

inserting a rounded endcap of the expandable interbody spacer between the two vertebrae so that a serrated outwardly facing surface of the first endplate faces a first vertebrae and a serrated outwardly facing surface of the second endplate faces a second vertebrae of the two vertebrae; and contracting a height between the first endplate and the second endplate by rotating, by the surgical screwdriver, the screwhead in a counterclockwise direction to force the first motion guider and the second motion guider apart.

17. An expandable interbody spacer system, comprising:

a first endplate including an outwardly facing surface, an inner facing surface and two opposing isosceles-trapezoidal-shaped sidewalls each configured with a central slot;

a second endplate including an outwardly facing surface and an inner facing surface and two opposing isosceles-trapezoidal-shaped sidewalls each configured with a central tab extension, wherein the second endplate is positioned directly opposite the first endplate, wherein each central tab of the second endplate is configured to slide into a respective central slot of the first endplate;

a motion assembly located between the opposing sidewalls of the first endplate and the opposing sidewalls of the second endplate, the motion assembly including:

a first motion guider having a smooth central cylindrical aperture;

a second motion guider having a threaded central cylindrical aperture;

a surgical screwdriver; and a screw having a screwhead and a partially threaded shank, wherein the partially threaded shank is positioned through the smooth central cylindrical aperture of the first motion guider and into the threaded central cylindrical aperture of the second motion guider, wherein clockwise rotation of the screwhead by the surgical screwdriver is configured to increase a height between the first endplate and the second endplate by drawing the first motion guider and the second motion guider together, wherein counterclockwise rotation of the screwhead by the surgical screwdriver is configured to decrease a height between the first endplate and the second endplate by moving the first and second motion guiders apart, wherein the first motion guider further comprises:

a rectangular cuboid body having a top face configured to contact the inner facing surface of the first endplate;

a bottom face configured to contact the inner facing surface of the second endplate;

a first wall which includes the smooth central cylindrical aperture, wherein the first wall faces towards a first wall of the second motion guider;

a second wall opposite the first wall;

a pair of bullet shaped endcaps attached to the second wall, wherein the pair of bullet shaped endcaps extends outwardly from the motion assembly;

a third wall having a rounded profile;

a fourth wall having a rounded profile opposite the third wall, wherein the third wall and the fourth wall are located between the top face and the bottom face;

a pair of slanted motion guiding grooves cut into each of the rounded profile of the third wall and the rounded profile of the fourth wall, wherein a first slanted motion guiding groove is configured to slant from a central width axis of the first wall towards the top face near the second wall, and a second motion guiding groove is configured to slant from a central width axis of the first wall towards the bottom face near the second wall, wherein a respective protrusion of a sidewall of the first endplate is configured to slide within the first slanted motion guiding groove and a respective protrusion of a sidewall of the second endplate is configured to slide within the second slanted motion guiding groove of the first motion guider;

the second motion guider further comprises:

a rectangular cuboid body having a top face configured to contact the inner facing surface of the first endplate;

a bottom face configured to contact the inner facing surface of the second endplate;

a first wall configured to face towards a first wall of the first motion guider;

a second wall opposite the first wall, wherein the threaded central cylindrical aperture is located within the rectangular cuboid body between the first wall and the second wall;

a rounded endcap attached to either side of the second wall, wherein the rounded endcap extends outwardly from the motion assembly;

a third wall having a rounded profile;

a fourth wall having a rounded profile opposite the third wall, wherein the third wall and the fourth wall are located between the top face and the bottom face; and a pair of slanted motion guiding grooves cut into each of the rounded profile of the third wall and the rounded profile of the fourth wall, wherein a first slanted motion guiding groove is configured to slant from a central width axis of the first wall towards the top face near the second wall, and a second motion guiding groove is configured to slant from a central width axis of the first wall towards the bottom face near the second wall, wherein a respective protrusion of a sidewall of the first endplate is configured to slide within the first slanted motion guiding groove and a respective protrusion of a sidewall of the second endplate is configured to slide within the second slanted motion guiding groove of the second motion guider.

* * * * *